US007025900B2

(12) United States Patent
Sidorenko et al.

(10) Patent No.: US 7,025,900 B2
(45) Date of Patent: Apr. 11, 2006

(54) PERYLENETETRACARBOXYLIC ACID DIBENZIMIDAZOLE SULFODERIVATIVES CONTAINING OXO-GROUPS IN THE PERYLENE CORE WHICH FORM PART OF A PARA-QUINOID SYSTEM OF BONDS, LYOTROPIC LIQUID CRYSTAL SYSTEMS AND ANISOTROPIC FILMS CONTAINING THE SAME, AND METHODS FOR MAKING THE SAME

(75) Inventors: Elena N. Sidorenko, Moscow (RU); Victor V. Nazarov, Odintsovo (RU)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 10/833,595

(22) Filed: Apr. 27, 2004

(65) Prior Publication Data
US 2005/0001202 A1 Jan. 6, 2005

Related U.S. Application Data

(60) Provisional application No. 60/482,779, filed on Jun. 25, 2003.

(51) Int. Cl.
*C09K 19/52* (2006.01)
*C09K 19/54* (2006.01)
*C07D 471/02* (2006.01)
*C07D 235/04* (2006.01)

(52) U.S. Cl. .................... 252/299.01; 428/1.1; 546/29; 548/304.4; 252/299.5

(58) Field of Classification Search ................ 428/1.1, 428/1.31; 252/299.01, 299.1, 299.5; 548/301.7, 548/313.7, 314.4, 304.4; 546/29
See application file for complete search history.

(56) References Cited

U.S. PATENT DOCUMENTS

| | | | |
|---|---|---|---|
| 2,553,961 A | | 5/1951 | Dreyer |
| 5,212,312 A | * | 5/1993 | Adam et al. .................. 546/32 |
| 5,739,296 A | | 4/1998 | Gvon et al. |
| 6,049,428 A | | 4/2000 | Khan et al. |
| 6,166,210 A | | 12/2000 | Langhals et al. |
| 6,174,394 B1 | | 1/2001 | Gvon et al. |
| 6,399,166 B1 | | 6/2002 | Khan et al. |
| 6,563,640 B1 | | 5/2003 | Ignatov et al. |
| 2003/0154909 A1 | | 8/2003 | Lazarev et al. |
| 2004/0058091 A1 | * | 3/2004 | Dutova et al. ................ 428/1.1 |
| 2004/0215015 A1 | * | 10/2004 | Nazarov et al. .............. 544/14 |

FOREIGN PATENT DOCUMENTS

| | | |
|---|---|---|
| DE | 31 45711 A1 | 5/1983 |
| EP | 0 961 138 A1 | 12/1998 |
| EP | 1 158 320 A2 | 11/2001 |

OTHER PUBLICATIONS

Bahadur, B., "Display Parameters and Requirements", *Liquid Crystals: Applications and Uses*, World Scientific, Singapore-New York, 1990, vol. 1, p. 110.

Bobrov, Y., et al., "Environmental and Optical Testing of Optiva Thin Crystal Film Polarizers", Proceedings of the $10^{th}$ SID Symposium "Advanced Display Technologies", Minsk, Republic of Belarus, Sep. 18-21, 2001, pp. 23-30.

Cormier, R.A., et al., "Self-Organization in Thin Films of Liquid Crystalline Perylene Diimides", *J. Phys. Chem.*, 1997, 101(51): 11004-11006, B.

Fiske, T., et al., "26.2: Molecular Alignment in /Crystal Polarizers and Retarders", Society of Information Display, Int. Symp. Digest of Technical Papers, Bost, MA, USA, May 19-24, 2002, pp. 866-869.

Iverson, I.K., et al., "Controlling Molecular Orientation in Solid Films via Self-Organization in the Liquid Crystalline Phase", *Langmuir*, 2002, ACS Publications, Columbus, OH, 18(9): 3510-5316.

Lydon, J., "A Well-Defined Family Distinct from Conventional Amphiphiles", *Handbook of Liquid Crystals*, Wiley—VCH, Weinheim, 1998, vol. 2B: pp. 981-1007.

Nazarov, V., et al., "Electronic Spectra of Aqueous Solutions and Films Made of Liquid Crystal Ink for Thin Film Polarizers", *Mol. Mater.*, 2001, 14(2): 153-163.

Quante, H., et al., "Synthesis of Soluble Perylenebisamidine Derivatives. Novel Long-Wavelength Absorbing and Fluorescent Dyes", *Chem. Mater.*, 1997, 9: 495-500.

Rogovik, V.I., "Perylene chemistry. Sulfonation of perylene-3,4,9,10-tetracarboxylic acid", *J. Org. Chem.*, USSR, 1972 (in Russian), Zhurnal Organicheskoi Khimii, VIII(2): 369-373.—English abstract.

* cited by examiner

*Primary Examiner*—Shean C. Wu
(74) *Attorney, Agent, or Firm*—Dorsey & Whitney LLP

(57) ABSTRACT

Anisotropic films based on sulfoderivatives of perylenetetracarboxylic acid dibenzimidazole (PTCA DBI) which contain oxo groups pendant to a perylene core. The oxo-groups, in combination with portions of the perylene core, form a quinoid system of bonds. The oxo substituted PTCA DBI sulfoderivatives form liquid crystal systems possessing high optical properties. Said liquid crystal systems can be applied onto various substrates to obtain optically isotropic or anisotropic, at least partially crystalline, films applicable in various fields.

27 Claims, 2 Drawing Sheets

PERYLENETETRACARBOXYLIC ACID DIBENZIMIDAZOLE SULFODERIVATIVES CONTAINING OXO-GROUPS IN THE PERYLENE CORE WHICH FORM PART OF A PARA-QUINOID SYSTEM OF BONDS, LYOTROPIC LIQUID CRYSTAL SYSTEMS AND ANISOTROPIC FILMS CONTAINING THE SAME, AND METHODS FOR MAKING THE SAME

CROSS REFERENCE TO RELATED APPLICATIONS

This U.S. non-provisional patent application claims the benefit, under 35 U.S.C. § 119(e), of U.S. provisional patent 60/482,779, filed on Jun. 25, 2003, entitled "A Lyotropic Liquid Crystal System Based On Perylenetetracarboxylic Acid Dibenzimidazole Sulfoderivatives, Containing Oxo-Groups In Perylene Core Which Are Involved In Para-Quinoid System Of Bands, Related Anisotropic Films, And Method For Making," the entire disclosure of which is incorporated herein by reference.

BACKGROUND OF THE INVENTION (1) Field of the Invention

The present invention relates generally to the fields of organic chemistry and optically anisotropic coatings. More specifically, the present invention relates to the synthesis of heterocyclic sulfoderivative compounds and the manufacture of optically anisotropic coatings based on these compounds.

(2) Description of Related Art

Modern technological progress requires development of optical elements based on new materials possessing specific, controllable properties. In particular, a necessary element in modern visual display systems is an optically anisotropic film with an optimum combination of optical and other characteristics for a particular device.

Various polymeric materials are known in the prior art for use in the manufacturing of optically anisotropic films. Films based on these polymeric materials acquire anisotropic optical properties through uniaxial extension and modification with organic dyes or iodine. In most applications, the base polymer is polyvinyl alcohol (PVA). Such films are described in greater detail in the monograph *Liquid Crystals: Applications and Uses*, B. Bahadur (ed.), World Scientific, Singapore-New York (1990), Vol. 1, p. 101. However, the low thermal stability of PVA-based films limits their application. It is desirable to find new materials and develop methods for the synthesis of optically anisotropic films possessing improved characteristics, in particular, higher heat resistance, more convenient synthesis, and better film-forming properties.

Organic dichroic dyes are a new class of materials gaining prominence in the manufacture of optically anisotropic films with high optical and working characteristics. Films based on these compounds are obtained through application of a layer of a liquid crystal (LC) aqueous dye solution, containing supramolecules composed of dye molecules, onto a substrate surface, followed by water evaporation. The resulting LC films acquire anisotropic properties either through preliminary mechanical ordering of the underlying substrate surface, as described in U.S. Pat. No. 2,553,961, or through subsequent application of external mechanical, electrical, magnetic or other orienting forces to the LC coating on the substrate, as described in U.S. Pat. Nos. 5,739,296 and 6,174,394. Basic properties of LC dye solutions are known in the prior art. However, extensive investigations into their application and the properties of related systems is a more recent development of the past decade. Recent studies have been motivated largely by industrial applications in liquid crystal displays (LCDs) and glazing. Dye supramolecules form a lyotropic liquid crystal (LLC) phase. In this phase, dye molecules generate supramolecular complexes having the form of columns—structural units of a mesophase. High ordering of dye molecules in the columns allows such mesophases to be used for obtaining oriented films characterized by a strong dichroism.

Another special property of dye molecules forming supramolecular LC mesophases is the presence of peripheral groups rendering these dyes water-soluble. The mesophases of organic dyes are characterized by specific structures, phase diagrams, optical properties, and dissolving capabilities. See J. Lydon, Chromonics, *Handbook of Liquid Crystals* (Wiley-VCH, Weinheim, 1998), Vol. 2B, pp. 981–1007.

By using dichroic dyes capable of forming LLC systems, it is possible to obtain films possessing a high degree of optical anisotropy. Such films exhibit the properties of E-type polarizers, which are related to peculiarities of the optical absorption of supramolecular complexes, and behave as retarders (phase-shifting devices) in the spectral regions where the absorption is insignificant. The phase-retarding properties of these anisotropic films are related to their birefringence (double refraction), that is, a difference in refractive indices measured in the direction of application of the LLC solution onto a substrate and in the perpendicular direction. Films formed from the LLC systems based on strong (light-fast) dye molecules are characterized by high thermal stability and light resistance.

The above properties of LLC systems account for the growing interest in these materials. New methods are extensively developed for obtaining films based on such organic dyes, the progress involving both optimization of the film application conditions and the search for new LLC systems. In particular, new LLC compositions for the synthesis of optically anisotropic films can be obtained by introducing modifiers, stabilizers, surfactants, and other additives to known dyes to improve characteristics of the films. See, for example, U.S. Pat. Nos. 5,739,296 and 6,174,394.

In recent years, there has been increasing demand for films possessing high optical anisotropy, characterized by improved selectivity in various wavelength ranges. Films with different positions of the absorption maximum, variable in a wide spectral range from infrared (IR) to ultraviolet (UV) regions, are needed. This has led to the development of an expanded assortment of compounds capable of forming LLC phases and films possessing the required properties. However, the number of dyes known to form stable lyotropic mesophases is still relatively small. Naturally, each new liquid-crystal dye becomes the object of thorough investigation.

Among water-soluble dichroic dyes capable of forming stable LLC phases, applicable in the manufacturing of optically anisotropic films, an important place belongs to disulfoderivatives of various organic dyes, including perylenetetracarboxylic acid (PTCA) dibenzimidazole (DBI) described in U.S. Pat. Nos. 5,739,296 and 6,174,394. PTCA dibenzimidazoles and diimides are widely used as dyes and pigments in various industries due to the high chemical, thermal, and photochemical stability of these compounds. These properties also explain the increased interest in these substances as potential materials for obtaining optically anisotropic films for LCDs and other optical devices.

The main difficulty hindering use of the above dyes is their poor solubility in water and some organic solvents. In order to provide the dyes with sufficient solubility in organic solvents, various substituents have been introduced into the molecules. Examples of such substituents are oxyethyl groups [see R. A. Cormier and B. A. Gregg, *Phys. Chem.* 101(51), 11004–11006 (1997)] and phenoxy groups [see H. Quante H. Y. Geerts, and K. Mullen, *Chem. Mater.* 6(2), 495–500 (1997)]. The solubility of perylene dyes has also been increased by amino groups [see I. K. Iverson, S. M. Casey, W. Seo, and S.-W. Tam-Chang, *Langmuir* 18(9), 3510–5316 (2002)] and sulfonic groups [see U.S. Pat. Nos. 5,739,296 and 6,174,394]. The best results were obtained with sulfonic groups, which provided for sufficient solubility and the formation of a stable LLC phase of perylene dyes.

The standard procedure of obtaining disulfoderivatives is as follows. To a certain volume of chlorosulfonic acid, one adds calculated amounts of PTCA DBI and oleum. Upon termination of the reaction, the mixture is colored and diluted with water. The precipitate is filtered, washed with hydrochloric acid, and dried. This yields water-soluble dibenzimidazole perylenetetracarboxydisulfonic acid, which is then dissolved in water and purified. An analysis of the system texture has shown that, beginning with a certain dye concentration, a stable hexagonal lyotropic mesophase is formed in a given temperature interval. Accordingly, a nematic phase is observed within a sufficiently narrow range of dye concentrations and temperatures. The boundaries of existence of isotropic phases, as well as two-phase transition regions, have been determined in this system.

Various dye compositions (inks) for the obtaining of polarizer films, based on PTCA DBI sulfoderivatives, have been described in patents. In particular, dyes having the following structural formula are known:

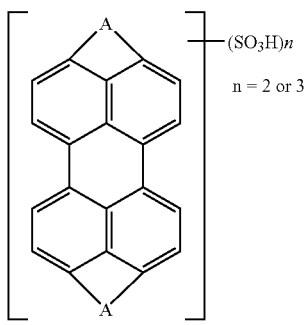

where

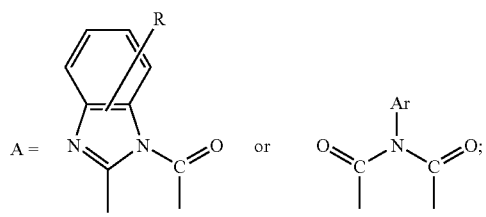

R=H, alkyl group, halogen or alkoxy group; and Ar is a substituted or nonsubstituted aryl radical. Such dyes, which are selective in the region of 550–600 nm, are described in U.S. Pat. No. 5,739,296.

Other dyes based on PTCA DBI have the formula:

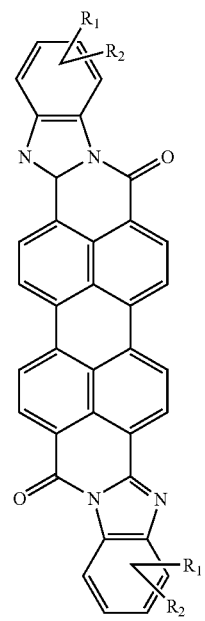

where $R_1$=H, 3(4)-$CH_3$, 3(4)-$C_2H_5$, 3(4)-Cl, 3(4)-Br; and $R_2$=4(5)-$SO_3H$. Such dyes, which are also selective in the region of 550–600 nm, are described in SU Patent No. 1,598,430.

LC blends of PTCA DBI sulfoderivatives where various modifying additives are introduced to improve the characteristics of anisotropic films are described in U.S. Pat. Nos. 5,739,296 and 6,174,394. Indanthrone disulfoderivatives with various substituents are described in U.S. Pat. Nos. 5,739,296 and 6,174,394. Compositions with various organic cations are described in published patent application EP 961138.

Thin anisotropic films obtained using LLC systems based on sulfoderivatives of various organic dyes, including perylene dyes, have been characterized with respect to their properties and structures. In particular, the properties of films obtained using perylene dye based LLC systems have been studied. See I. K. Iverson, S. M. Casey, W. Seo, and S.-W. Tam-Chang, Controlling Molecular Orientation in Solid-Crystalline Phase, *Langmuir* 18(9), 3510–3516 (2002). All films were reported to possess a high degree of optical anisotropy.

The properties of thin anisotropic films obtained using an LLC system based on sulfoderivatives of organic dyes has been reported. See T. Fiske, L. Ignatov, P. Lazarev, V. Nazarov, M. Paukshto, Molecular Alignment in Crystal Polarizers and Retarders, *Society for Information Display, Int. Symp. Digest of Technical Papers* (Boston, Mass., May 19–24, 2002), p. 566–569. It was established that these films possess at least a partially crystalline structure. Optically anisotropic films can be obtained on substrates of glass, plastic, or any other material. The Violet dye used for the formation of these anisotropic films represents a blend of cis and trans isomers. See V. Nazarov, L. Ignatov, K. Kienskaya, Electronic Spectra of Aqueous Solutions and Films Made of Liquid Crystal Ink for Thin Film Polarizers, *Mol. Mater.* 14(2), 153–163 (2001). Possessing high optical characteristics, with a dichroic ratio reaching 25–30, these films can be used as polarizers. See Y. Bobrov, L. Blinov, L. Ignatov, G.

King, V. Lazarev, Y.-D. Ma, V. Nazarov, E. Neburchilova, N. Ovchinnikova, S. Remizov, Environmental and Optical Testing of Optiva Thin Crystal Film™ Polarizers, *Proceedings of the 10th SID Symposium "Advanced display technologies"*, (Minsk, Republic of Belarus, Sep. 18–21, 2001), p. 23–30.

Methods for obtaining of such films, including those with high degree of crystallinity, are described in PCT Publication WO 02/063,660.

All of the aforementioned PTCA DBI sulfoderivatives are capable of forming LLC phases. Anisotropic films obtained using such LLC systems possess high optical characteristics and show good performance as polarizers.

However, one of the main disadvantages of the known water-soluble PTCA DBI sulfoderivatives is the difficulty of obtaining related anisotropic films possessing reproducible (from batch to batch and on different substrates in the same batch) and homogeneous (over the substrate surface) properties. The existing film application technologies require the process parameters (concentration, temperature, etc.) to be thoroughly selected and strictly followed. However, even in cases when all the conditions of film formation are strictly obeyed, random local violation of the coating structure is still possible. This is related to a certain probability of the formation of misorientation zones and micro defects as a result of non-uniform micro and macro crystallization processes in the course of solvent removal upon LLC system application onto a substrate surface. In addition, LLC systems based on the known dyes are characterized by increased probability of non-uniform thickness of the applied coating, which also decreases reproducibility of the film parameters. The aforementioned disadvantages complicate the formation of films possessing high optical characteristics, make the technology insufficiently reproducible, and require most of the technological parameters to be thoroughly selected and strictly followed in each stage, from application to drying.

BRIEF SUMMARY OF THE INVENTION

The disclosed invention provides new water-soluble sulfoderivatives of perylenetetracarboxylic acid dibenzimidazole (PTCA DBI) and optical elements based on these compounds. It has been discovered that certain substituents, when introduced at certain positions on the PTCA DBI sulfoderivative, increase the homogeneity of the crystallization and drying processes and, thereby, increase the yield of films formed with reproducible characteristics.

Specifically, in one embodiment, PTCA DBI sulfoderivatives are disclosed that contain oxo-groups pendant to a perylene core which are involved in a quinoid system of bonds. The oxo substituted PTCA DBI sulfoderivatives are capable of forming stable LLC mesophases.

The oxo substituted PTCA DBI sulfoderivatives can be used to obtain anisotropic, at least partially crystalline films, with reproducibly high optical characteristics. Therefore, another embodiment of the disclosed invention is the formation of anisotropic films based on the oxo substituted, PTCA DBI sulfoderivatives which can be used as polarizing films. The invention expands the assortment of compounds that absorb in the visible spectral range and are capable of forming stable LLC phases with increased stability.

Accordingly, the invention provides new organic compounds, the LLC phases of which possess increased stability over a broad range of concentrations, temperatures, and pH values. Furthermore, the invention provides new organic compounds that simplify the process of film formation and allow the use of available commercial equipment for the application of layers, and which ensure the formation of films with reproducible parameters.

DETAILED DESCRIPTION OF THE INVENTION (1) Definitions

As used herein, the following terms have the following meanings:

The phrases "sulfonated" and "sulfoderivative" refer to the presence of one or more sulfo substituents.

The word "sulfo" refers to an —$SO_3^-$ or —$SO_3H$ substituent.

The phrase "perylene tetracarboxylic acid dibenzimidazole," abbreviated PTCA DBI, means one of the following structures (A) or (B):

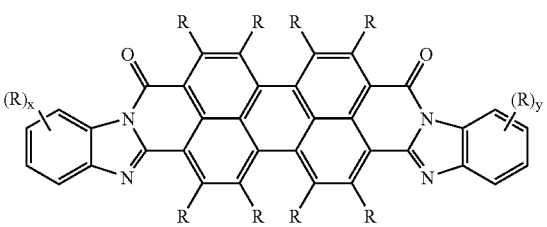

(A)

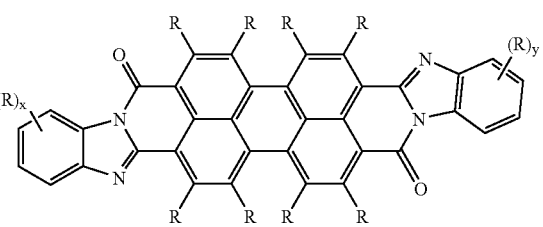

(B)

where each R is a substituent that can be the same or different and can be fused with a neighboring R group to form a bridge and where x and y are integers ranging from 1 to 4.

The phrase oxo group means =O.

The phrase "perylene core" means the following moiety (1) which appears, for example, within a PTCA DBI:

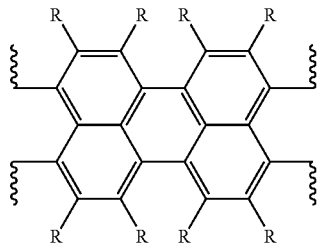

(I)

where each R is a substituent that can be the same or different and can be fused with neighboring R group to form a bridge.

The phrase "para-quinoid" or "para quinoid system of bonds" means one of the following moieties (m) or (n):

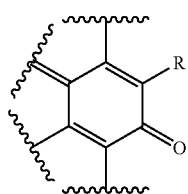

(m)

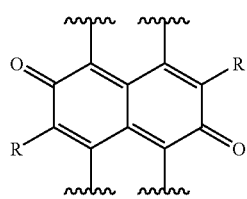

(n)

(2) Description

The PTCA DBI sulfoderivatives of the present invention contain oxo-groups pendant to the perylene core. The oxo-groups and portions of the perylene core form a para-quinoid system of bonds. The oxo substituted PTCA DBI sulfoderivatives comprise, for example, any one of the general structural formulae I to VII set forth below.

Figure 1:
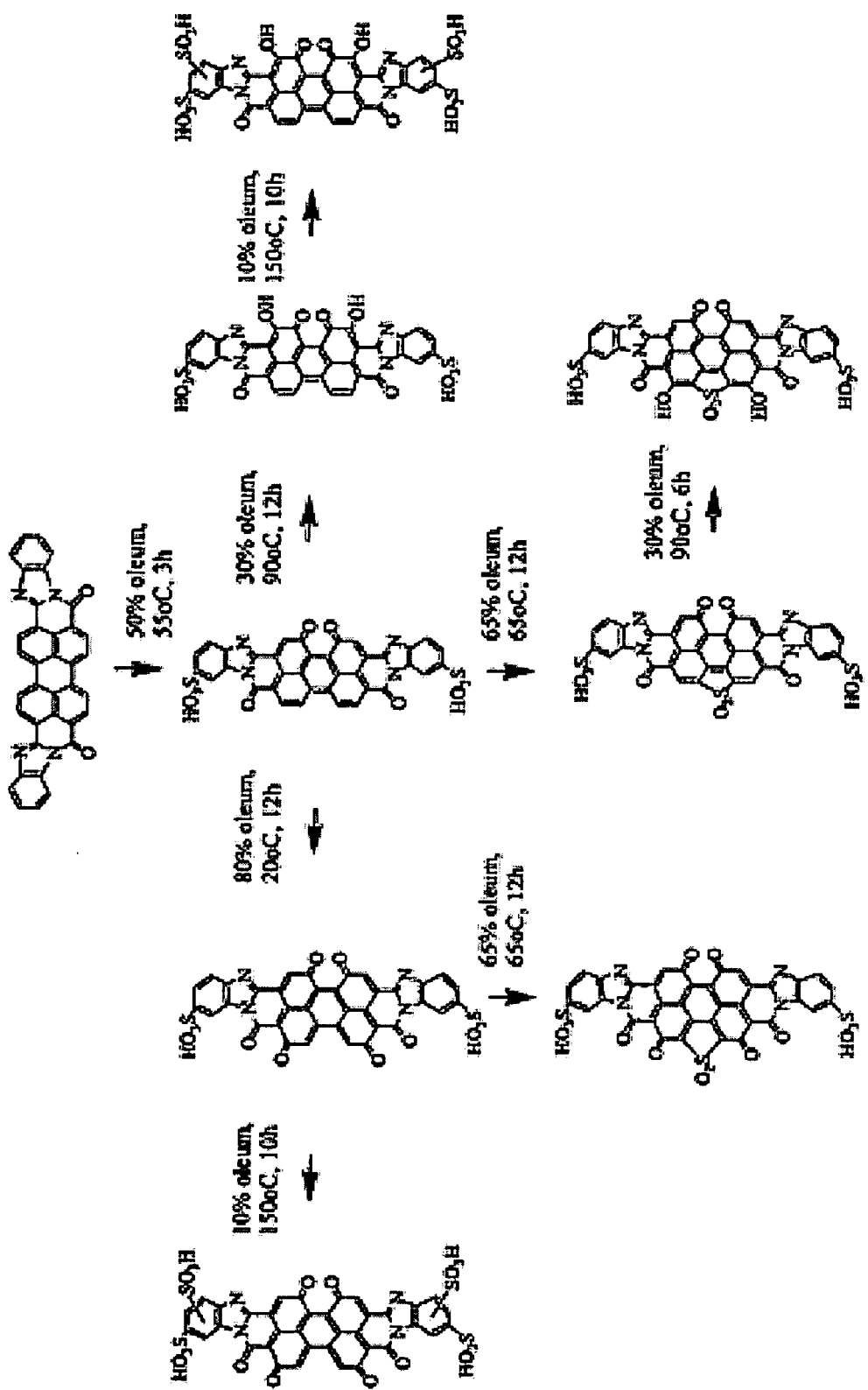
FIG. 1 is a schematic diagram of the conversion of PTCA DBI, through oxidation, to sulfoderivatives containing oxo-groups on the perylene core that form part of a para-quinoid system of bonds.

The oxo substituted PTCA DBI sulfoderivatives can be cis or trans isomers synthesized by any of the known methods. In particular, as illustrated in FIG. 1, the oxo substituted PTCA DBI sulfoderivatives can be obtained through sulfonation of PTCA DBI under various conditions.

Figure 2:
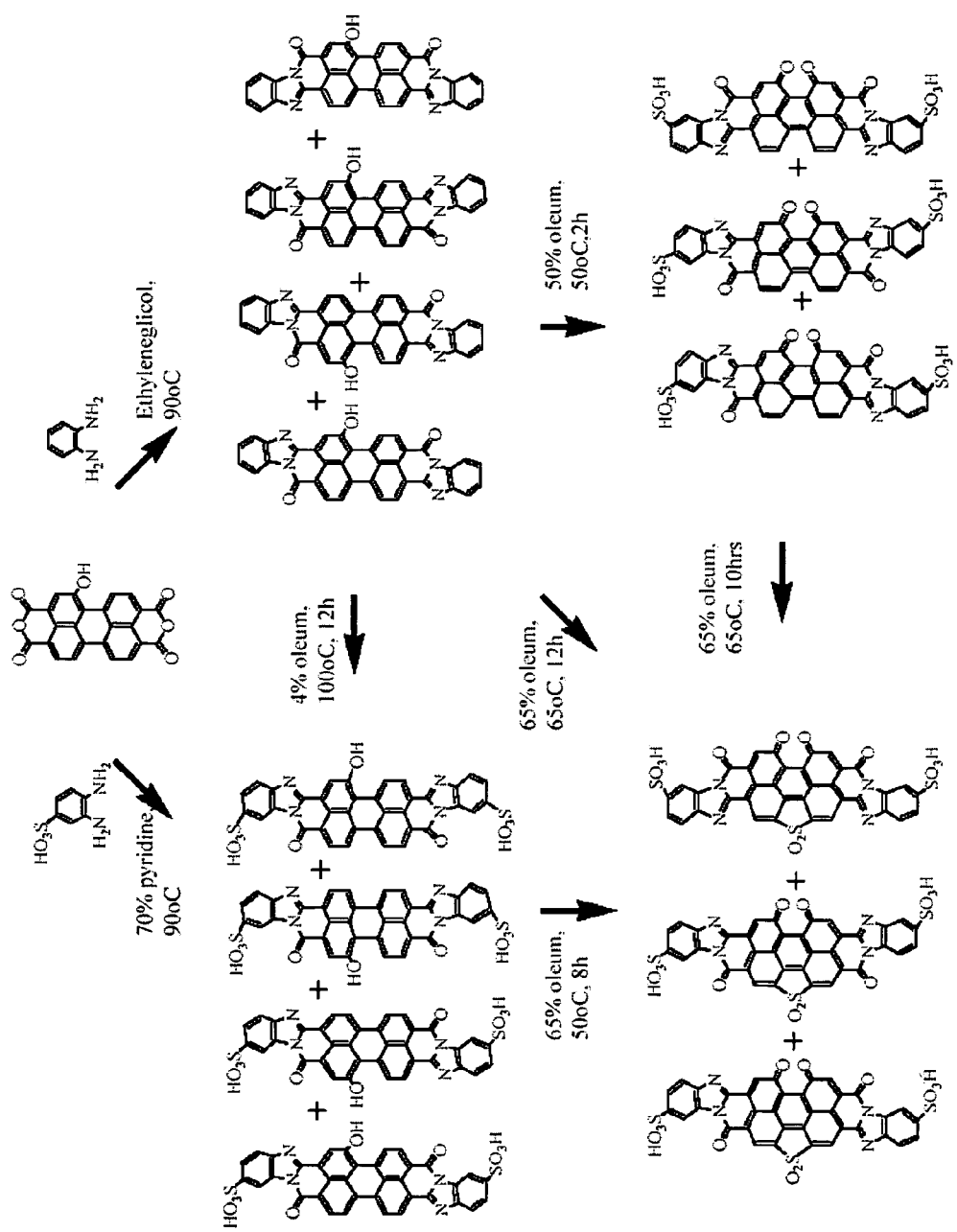
FIG. 2 illustrates the synthesis of PTCA DBI sulfoderivatives, which contain oxo-groups on the perylene core that form para-quinoid fragments, from PTCA hydroxyderivatives starting with 1-hydroxy PTCA.

In addition, the oxo substituted PTCA DBI sulfoderivatives can be obtained from PTCA hydroxy-derivatives through condensation with o-phenylenediamine or with o-phenylenediamine sulfonate, followed by oxidation and in some embodiments by further sulfonation. FIG. 2 schematically presents pathways for synthesizing oxo substituted PTCA DBI compounds from a PTCA hydroxyderivative of known structure.

Alternatively, individual oxo substituted PTCA DBI sulfoderivatives can be obtained through fractionation of their mixtures.

Mixtures of oxo substituted PTCA DBI sulfoderivatives can be obtained through isomerization of pure compounds.

The oxo substituted PTCA DBI sulfoderivatives, including those of the general structural formulae I to VII set forth below, can be synthesized provided certain pre-selected conditions are obeyed. In order to obtain the target compounds, it is sufficient to determine the initial concentrations of reactants and the technological conditions of synthesis. The most significant parameters are the concentrations of initial reactants, temperature, and reaction duration. These parameters determine the result of synthesis, the product yield, and the ratio of various oxo substituted PTCA DBI derivatives (e.g., formulas I–VII) and their isomers in the reaction mass.

Another aspect of the present invention is the development of new organic compounds whose solutions are characterized by the optimum hydrophilic-hydrophobic balance. This balance favorably influences the size and shape of supramolecular complexes formed in such systems, as a well as the degree of molecular order in these complexes. These properties provide for the required solubility of the compounds under consideration and, simultaneously, ensure high stability of the LLC phases based on these compounds. As a result, reproducibility of the film parameters increases and the production technology simplifies, because requirements for selecting and maintaining the optimum technological conditions on various production stages become less stringent. In addition, optical characteristics of the new films are improved because the planar molecules of the oxo substituted PTCA DBI sulfoderivatives are more homogeneity oriented with respect to the substrate, and the dipole moments of electron transitions (lying in the planes of molecules) are better aligned in the direction determined by external orienting factors.

The above objectives are achieved using the disclosed water-soluble oxo substituted PTCA DBI sulfoderivatives, which are original compounds not previously described in the literature. The technical result is ensured by using chemical compounds characterized by the disclosed structural formula, liquid crystal systems based on these compounds, and optical anisotropic films manufactured using this system.

The objective of the disclosed invention is ensured by using sulfonated cis and/or trans derivatives of perylenetetracarboxylic acid dibenzimidazole containing oxo-groups in the perylene core that, together with portions of the perylene core, form a para-quinoid system of bonds. Illustrative compounds comprise one of the following general structural formula I–VII:

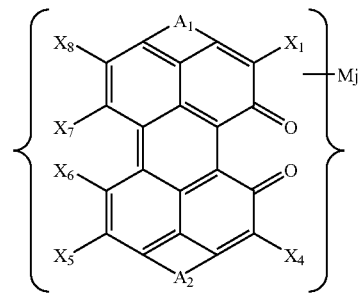

I

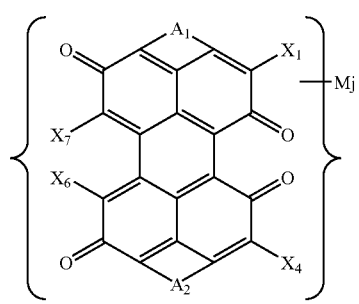

II

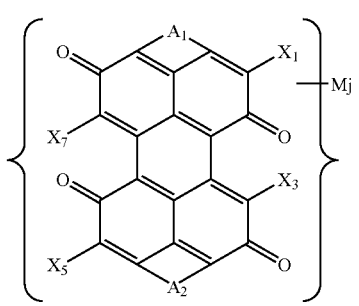

III

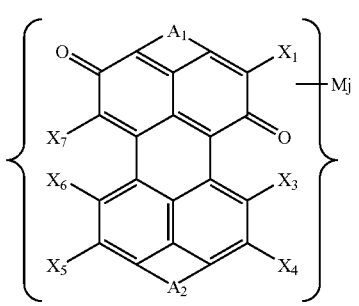

IV

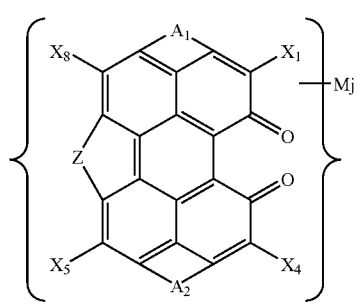

V

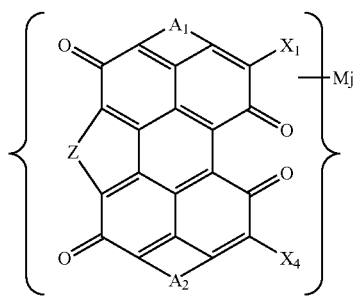

VI

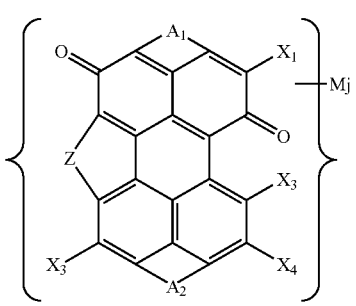

VII where $A_1$ and $A_2$ are, independently, identical or non-identical fragments comprising the following general structural formula:

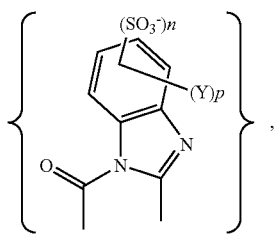

where $X_1$, $X_3$, $X_4$, $X_5$, $X_6$, $X_7$, and $X_8$ are substituents selected, independently, from the group including —H, —OH, —SO$_3$H, such that substituents $X_6$ and $X_7$ may interact with each other to form a bridge Z; where Z is a bridge selected from the series —O—, —SO$_2$—, and —SO$_2$—O—; where each Y is a substituent selected, independently, from the series —H, —Cl, —F, —Br, Alk, —OH, —OAlk, —NO$_2$, and —NH$_2$; where n is an integer in the range of 0, 1, and 2, such that at least one of fragments $A_1$ and $A_2$ comprises at least one sulfo group; where p is an integer in the range of 0, 1, 2, 3 and 4; where each M is counterion; where j is the number of counterions in the dye molecule, which can be fractional if one or more counterions belong to several molecules; and where, when n>1, different counterions M can be involved.

All the compounds of formulas I–VII are capable of forming stable LLC phases, both individually and in admixture with other compounds of the group, as well as in admixture with other dichroic dyes capable of forming LLC phases and/or with other substances that are non-absorbing (colorless) or weakly absorbing in the visible range and capable of forming LLC phases. After removal of the solvent, the LLC phase forms an anisotropic, at least partially crystalline, film with reproducibly high optical characteristics.

The oxo substituted PTCA DBI sulfoderivatives exhibit, in aqueous solutions, maximum optical absorption in a wavelength interval of 530–600 nm. The introduction of substituents such as Cl, F, Br, Alk, and OAlk does not significantly shift the absorption band as compared to the unsubstituted molecules. The introduction of amino and hydroxy groups broadens the absorption band and changes the character of the absorption spectrum. By varying the number of sulfonic groups and the number and character of substituents in the oxo substituted PTCA DBI sulfoderivative, it is possible to control the hydrophilic-hydrophobic balance of molecular aggregates formed in LLC solutions and to change the solution viscosity. The technical result of the invention is achieved irrespective of the number and types of substituents indicated in the structures I–VII.

In structures I-VII, counterions M can be represented by various cations from the series $H^+$, $NH^+_4$, $K^+$, $Li^+$, $Na^+$, $Cs^+$, $Ca^{++}$, $Sr^{++}$, $Mg^{++}$, $Ba^{++}$, $Co^{++}$, $Mn^{++}$, $Zn^{++}$, $Cu^{++}$, $Pb^{++}$, $Fe^{++}$, $Ni^{++}$, $Al^{+++}$, $Ce^{+++}$, $La^{+++}$, etc., as well as by combinations of such cations.

The oxo substituted PTCA DBI sulfoderivatives are capable of forming stable lyotropic liquid crystal systems. Liquid crystal solutions (systems) comprising individual oxo substituted PTCA DBI sulfoderivatives of structural formulas I–VII, as well as mixtures of such compounds, can be prepared by any conventional method.

The liquid crystal solutions (systems) of individual oxo substituted PTCA DBI sulfoderivatives of general structural formulas I–VII, as well as mixtures of such compounds, can be applied onto a substrate surface and oriented by any known method, such as the methods described in U.S. Pat. Nos. 5,739,296, 6,174,394 and 6,563,640 the disclosures of which are hereby incorporated by reference in their entirety. According to the disclosures in the aforementioned patents, the desired orientation can be provided, for example, by applying mechanical shear stress or an electric or magnetic field. For better substrate wetting and optimization of the rheological properties of a liquid crystal system, the solution can be modified by adding plasticizing water-soluble polymers and/or anionic or non-ionic surfactants. In addition, the system may comprise water-soluble, low-molecular-weight additives. All additives are selected so as not to destroy the alignment properties of the liquid crystal system. Subsequent removal of the solvent from the oriented film leads to the formation of an optically anisotropic polycrystalline film with a thickness ranging from 0.2 to 1.2 microns.

The films according to the disclosed invention are characterized by an increase in the reproducibility of the parameters from batch to batch, between different films in the same batch, and over the surface of one film, as compared to the films obtained, for example, from disulfo PTCA DBI.

Thus, the disclosed oxo substituted PTCA DBI sulfoderivatives are capable of forming a lyotropic liquid crystal phase and can be used to obtain anisotropic films possessing highly reproducible optical characteristics.

The disclosed oxo substituted PTCA DBI sulfoderivatives are capable of forming optically isotropic or anisotropic films.

The disclosed oxo substituted PTCA DBI sulfoderivatives are capable of forming at least partially crystalline films. The films exhibit an interplanar spacing in the crystals in the range of approximately 3.1 Å to 3.7 Å along one of the optical axes. The interplanar spacing is easily fixed with standard methods, such as for example X-ray diffraction.

The disclosed oxo substituted PTCA DBI sulfoderivatives are capable of forming polarizing and/or birefringent (double refraction) films.

The disclosed oxo substituted PTCA DBI sulfoderivatives can be part of the composition of optically isotropic or anisotropic, polarizing and/or phase-retarding and/or birefringent films. The material of an optically isotropic or anisotropic film may include at least two compounds of formulae I to VII, and/or a mixture of at least two compounds of at least one of formulae I to VII, comprising at least two different substituents.

The technical result of the disclosed invention is also obtained an aqueous liquid crystal system (sometimes called a "water-based ink composition") comprising an individual member selected from the disclosed oxo substituted PTCA DBI sulfoderivatives of structural formulae I to VII, or a mixture of at least two such compounds. The disclosed liquid crystal system is based on water, or a mixture of water and an organic solvent that is either miscible with water in any proportion or characterized by limited miscibility with water. The content of the disclosed oxo substituted PTCA DBI sulfoderivatives either individually, or in admixture, in the disclosed liquid crystal system ranges from 3 to 40 mass %, and most typically ranges from 7 to 20 mass %. The disclosed liquid crystal system may also comprise up to 5% mass of surfactants and/or plasticizers.

The content of particular oxo substituted PTCA DBI sulfoderivatives in the disclosed liquid crystal system may vary, depending on the required properties, within the following limits:

compounds of formulas I and/or V, from 0 to 99 mass %, most favorably within 0–70 mass %;

compounds of formula II and/or VI, from 0 to 99 mass %, most favorably within 0–50 mass %;

compounds of formula IV and/or VII, from 0 to 50 mass %, most favorably within 0–20 mass %;

compounds of formula III, from 0 to 99 mass %, most favorably within 0–20 mass %.

The disclosed liquid crystal system may additionally comprise at least one water-soluble organic dye or a colorless organic compound capable of participating in the formation of a lyotropic liquid crystal phase.

The disclosed liquid crystal system may include compounds selected from two or more of formulae I to VII and/or two or more compounds selected from one of formulae I to VII that comprise at least two different substituents.

The technical result of the disclosed invention is also obtained by an optically anisotropic film comprising either individual oxo substituted PTCA DBI sulfoderivatives of the general structural formulas I–VII, or a mixture of such compounds. The optically anisotropic film may additionally comprise a different organic dye or some colorless compound. An optically anisotropic film according to this invention can be obtained by applying a liquid crystal system onto a substrate, followed by orienting action and drying. The anisotropic film is at least partially crystalline.

The film material according to this invention includes at least two compounds selected from different formulae I to VII and/or at least two compounds within one of formulae I to VII comprising at least two different substituents.

FIG. 1 and FIG. 2 present possible methods of manufacturing. The disclosed compounds can be manufactured by the method of sulfonation (FIG. 1) and by the condensation and consequent oxidation (FIG. 2). The experimental results set forth below present some examples of both methods of manufacture. The examples are intended for illustration purposes only, and are not intended to limit the scope of the invention.

EXAMPLE 1

Synthesis of Isomeric DBI PTCA Dioxo-Disulfoacids

Stage 1a. Condensation of monohydroxyPTCADA with o-phenylenediamine

A suspension of 1 g of monohydroxyPTCADA prepared by the known way (see J. Org. Chem., USSR, 1972, VIII, 369) and 1.6 g of o-phenylenediamine in 30 ml of ethylene glycol was heated at 90° C. for 10 hours. The precipitate was separated by filtration and washed with ethanol. Yield, 1.3 g of compounds of the structural formulas

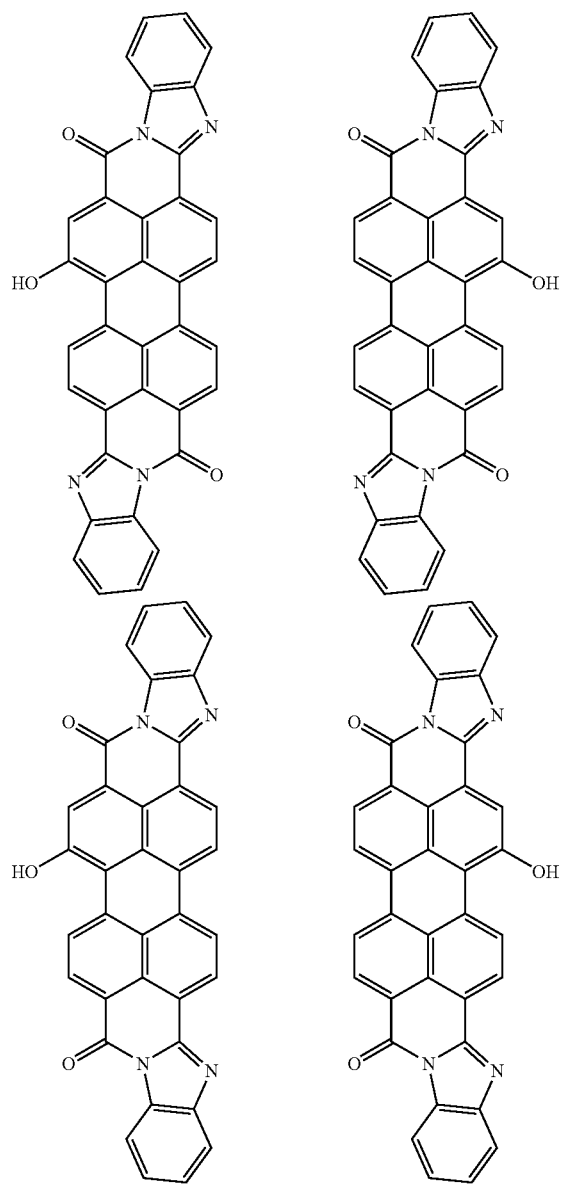

Mass spectrum (VISION 2000, negative reflection mode): m/z, 551.7; mol. wt., 552.54.

Stage 1b. Synthesis of a Mixture of Isomeric DBI PTCA Dioxo-Disulfoacids

The product of stage 1a (1 g) was sulfonated in 5 ml of 50% oleum for 2 hours at 50° C. and then the reaction mass was diluted with sulfuric acid and then with water to obtain 55% sulfuric acid. The precipitate was separated by filtration and washed with acetic acid. Yield, 1.1 g of compounds of the structural formulas

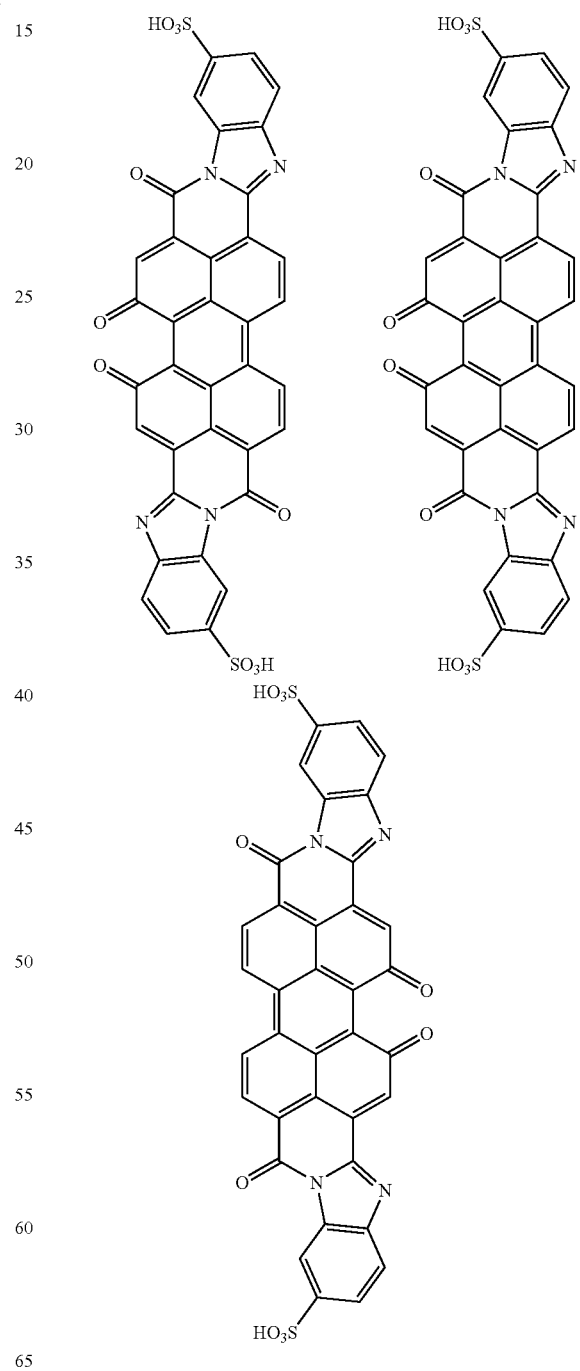

Mass spectrum (VISION 2000, negative reflection mode): m/z, 726.2; mol. wt., 726.65.

Stage 1c. Preparation of Individual Isomers of DBI PTCA Dioxo-Disulfoacids

A mixture of isomers from stage 1b (1 g) was dissolved in 20 ml of sulfuric acid and diluted with water to obtain the 65% sulfuric acid. The precipitate was separated by filtration and washed with acetic acid. Yield, 0.5 g of compounds of the structural formula

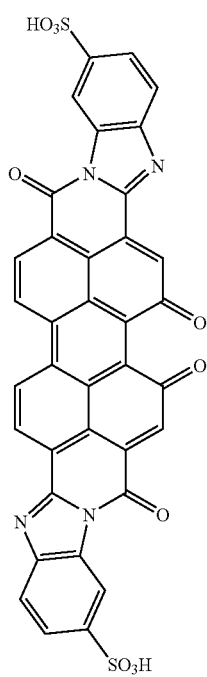

Mass spectrum (VISION 2000, negative reflection mode): m/z, 726.5; mol. wt., 726.65; elemental analysis, found (%): C, 59.13; 59; 48; H, 1.87; 1.90; N, 7.51; 7.38; S, 8.66; 9.07 $C_{36}H_{14}N_4O_{10}S_3$; anal. calcd. for $C_{36}H_{14}N_4O_{10}S_2$ (%): C, 59.50; H, 1.94; N, 7.71; O, 22.02; S, 8.83; IR spectrum (FSM-1201 Fourier-transform IR spectrometer, thin film on KRS-5 window) (ν, cm−1): 1229.0, 1179.7 (sulfonic groups), 1073.6, 1033.2 (sulfonic groups), 1670.6 (carbonyl); electronic absorption spectrum (Ocean PC2000, aqueous solution) (λmax, nm): 325, 375, 540.

On dilution of mother liquid with water to the sulfuric acid concentration 45% another isomer was precipitated. It also was separated by filtration and washed with acetic acid. Yield, 0.4 g of compounds of the structural formulas

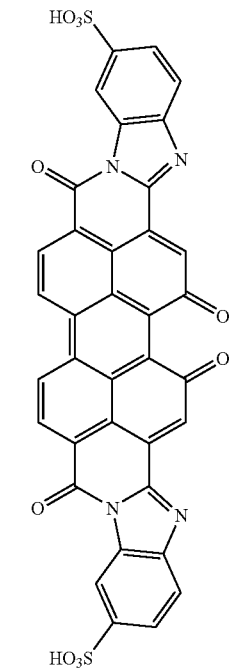

Mass spectrum (VISION 2000, negative reflection mode): m/z, 726.5; mol. wt., 726.65; electronic absorption spectrum (Ocean PC2000, aqueous solution) (λmax, nm): 325, 355, 375, 550.

EXAMPLE 2

Synthesis of Isomeric DBI PTCA Dioxo-Sulfon-Disulfoacids

Stage 2a. Synthesis of a Mixture of Isomeric DBI PTCA Dioxo-Sulfon-Disulfoacids

The product of stage 1a (1 g) was sulfonated in 5 ml of 65% oleum for 12 hours at 65° C. and then the reaction mass was diluted with sulfuric acid and then with water to obtain 45% sulfuric acid. The precipitate was separated by filtration and washed with acetic acid. Yield, 1.4 g of compounds of the structural formulas

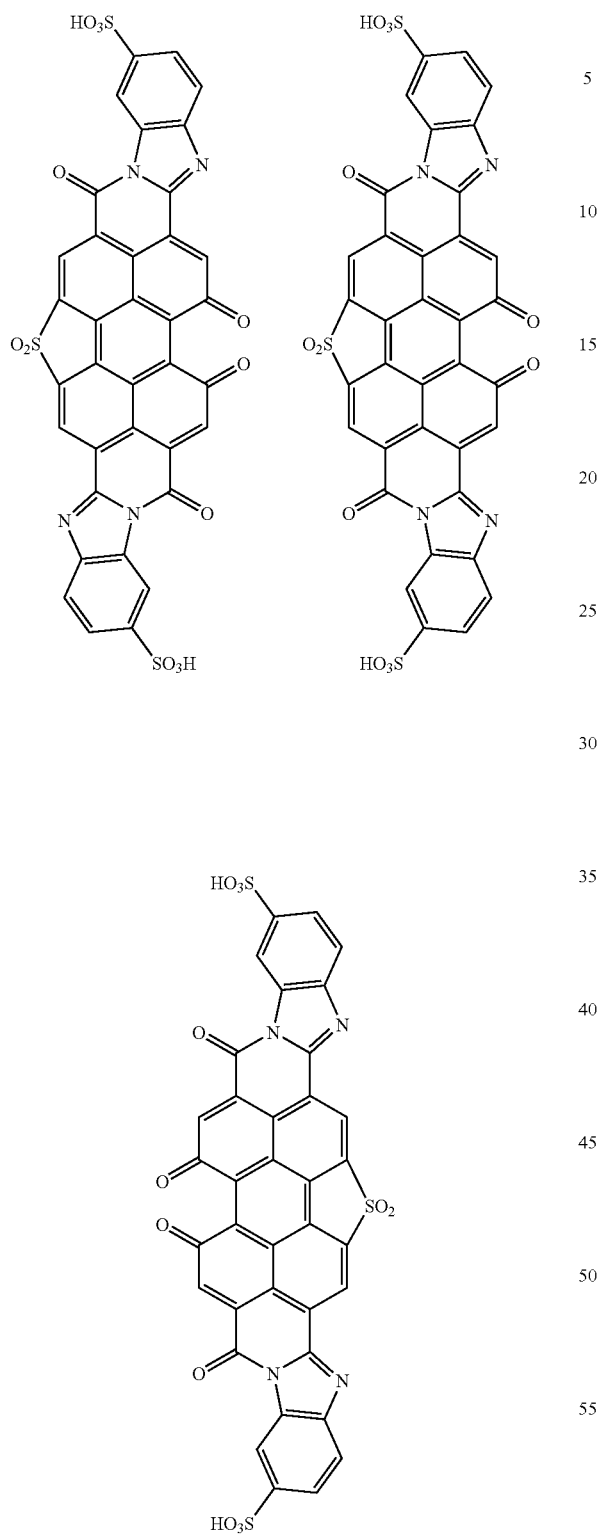

Stage 2b. Preparation of Individual Trans-Isomers of DBI PTCA Dioxo-Sulfon-Disulfoacids A mixture of isomers from stage 2a (1 g) was dissolved in 20 ml of sulfuric acid and diluted with water to obtain the 65% sulfuric acid. The precipitate was separated by filtration and washed with acetic acid. Yield, 0.5 g of compounds of the structural formula

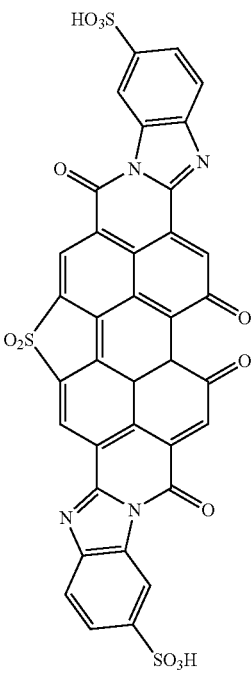

Mass spectrum (VISION 2000, negative reflection mode): m/z, 789.2; mol. wt., 788.7; elemental analysis, found (%): C, 54.22; 54; 45; H, 1.44; 1.46; N, 7.01; 7.19; S, 12.32; 12.10 $C_{36}H_{14}N_4O_{10}S_3$; anal. calcd. for $C_{36}H_{12}N_4O_{12}S_3$ (%): C, 54.82; H, 1.53; N, 7.10; O, 24.34; S, 12.20; IR spectrum (FSM-1201 Fourier-transform IR spectrometer, thin film on KRS-5 window) (v, cm−1): 1228.9, 1179.4 (sulfonic groups), 1074.0, 1027.0 (sulfonic groups), 1324.0 (sulfone), 1699.6 (carbonyl); electronic absorption spectrum (Ocean PC2000, aqueous solution) (λmax, nm): 325, 375, 540, 600.

Stage 2c. Preparation of Individual Cis-Isomers of DBI PTCA Dioxo-Sulfon-Disulfoacids On dilution of mother liquid with water to the sulfuric acid concentration 45% another isomer was precipitated. It also was separated by filtration and washed with acetic acid. Yield, 0.4 g of compounds of the structural formulas Mass spectrum (VISION 2000, negative reflection mode): m/z, 789.2; mol. wt., 788.7; electronic absorption spectrum (Ocean PC2000, aqueous solution) (λmax, nm): 325, 375, 550, 590.

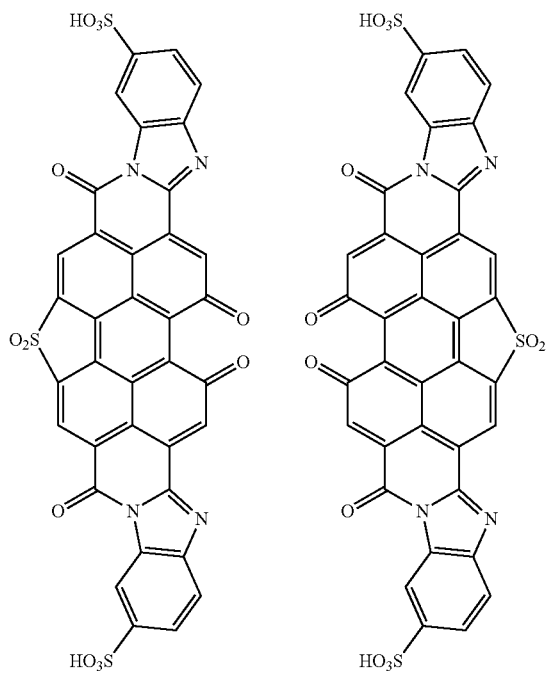

Mass spectrum (VISION 2000, negative reflection mode): m/z, 789.2; mol. wt., 788.7; electronic absorption spectrum (Ocean PC2000, aqueous solution) (λmax, nm): 325, 355, 375, 550, 580.

EXAMPLE 3
Synthesis of Isomeric DBI PTCA Dioxo-Sulfon-Disulfoacids from DBI PTCA Disulfoacids

Stage 3a. Condensation of MonohydroxyPTCADA with o-phenylenediamine Sulfonate A mixture of monohydroxyPTCADA (1 g) and 1.5 g of o-phenylenediamine sulfonate in 30 ml of 70% aqueous pyridine was heated at 90° C. for 8 hours. The precipitate was separated by filtration and washed with an aqueous ethanol solution. Yield, 1.2 g of compounds of the same structural formulas

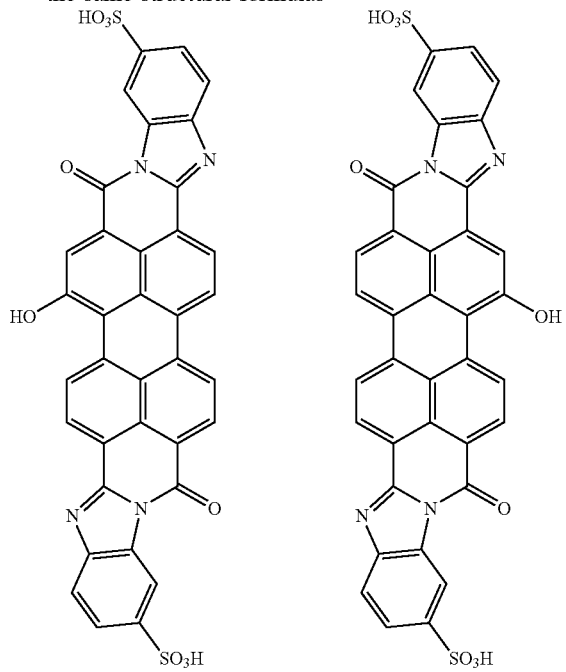

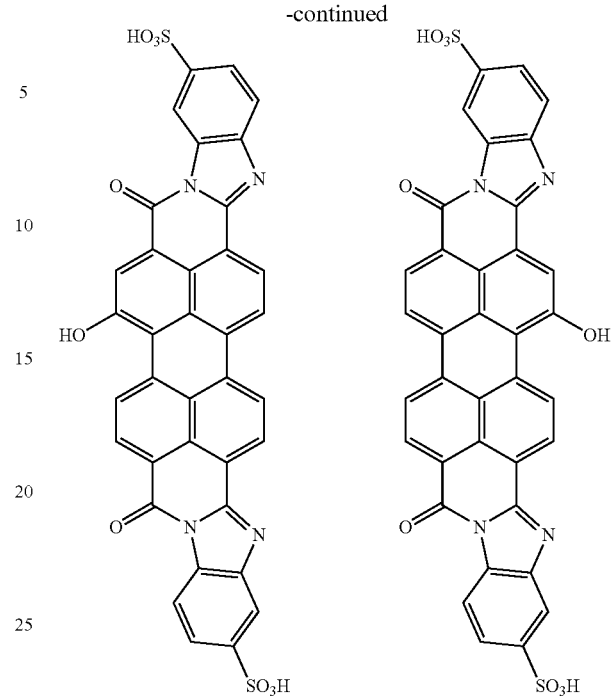

Mass spectrum (VISION 2000, negative reflection mode): m/z, 711.4; mol. wt., 712.67.

Stage 3b. Oxidation and Sulfonation of PTCADBI Monohydroxyderivatives with Oleum A mixture of monohydroxyPTCADBI (1 g) was heated in 30 ml of 65% oleum at 50° C. for 8 h. Then the reaction mass was diluted with sulfuric acid and with water to obtain 55% sulfuric acid. The precipitate was separated by filtration and washed with acetic acid. Yield, 1.4 g of compounds similar to the product from the example 2a of the structural formulas

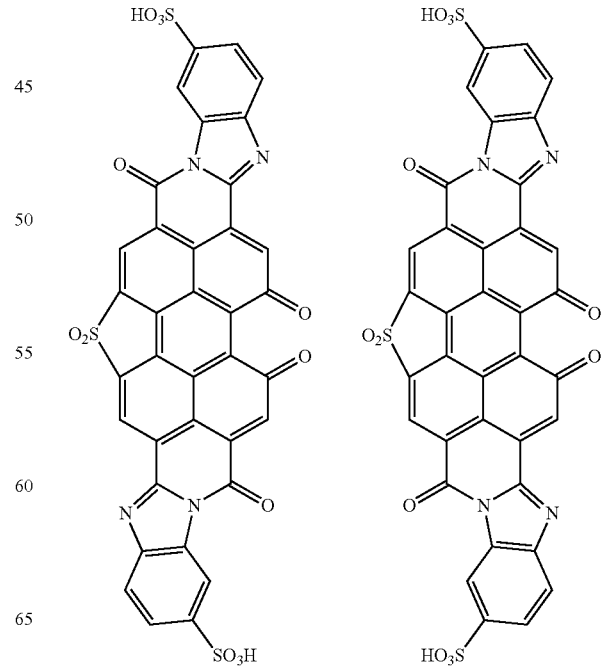

-continued

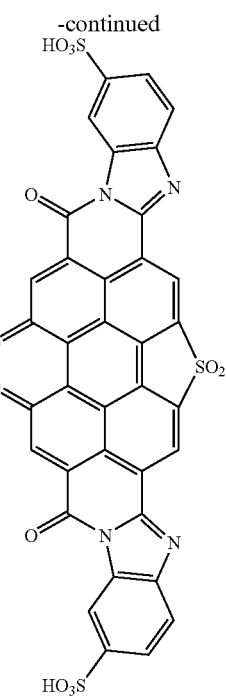

EXAMPLE 4

Synthesis of Trans-DBI PTCA Dioxo-Disulfoacid

Trans-DBI PTCA (1 g) was sulfonated in 100 ml of 55% oleum for 3 hours at 50° C. and then the reaction mass was diluted with sulfuric acid and with water to obtain 65% sulfuric acid. The precipitate was separated by filtration and washed with acetic acid. Yield, 0.9 g of compound which has the same structure that the product from the example 1c and corresponds to the structural formula

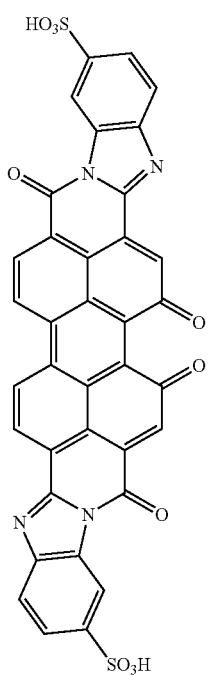

EXAMPLE 5

Synthesis of Trans-DBI PTCA Dioxo-Sulfon-Disulfoacids

Stage 5a. Sulfonation of Trans-DBI PTCA Dioxo-Disulfoacid

The product of example 4 (1 g) was sulfonated in 50 ml of 65% oleum for 10 hours at 65° C. and then the reaction mass was diluted with sulfuric acid and then with water to obtain 45% sulfuric acid. The precipitate was separated by filtration and washed with acetic acid. Yield, 1 g of compounds which has the same structure that the product from the example 2b and corresponds to the structural formula

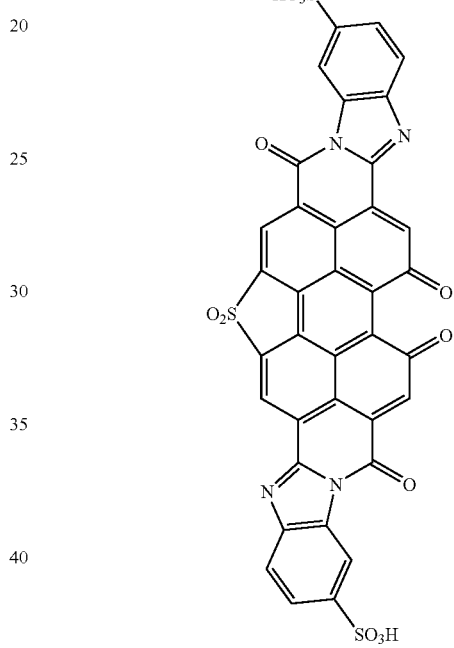

Stage 5b. Sulfonation of Trans-DBI PTCA

Trans-DBI PTCA (1 g) was sulfonated in 100 ml of 65% oleum for 12 hours at 60–55° C. and then the reaction mass was diluted with sulfuric acid and with water to obtain 65% sulfuric acid. The precipitate was separated by filtration and washed with acetic acid. Yield, 1.2 g of compound of the same structure as was obtained in the example 5a.

EXAMPLE 6

Synthesis of Cis-DBI PTCA Dioxo-Disulfoacid

Cis-DBI PTCA (1 g) was sulfonated in 30 ml of 50% oleum for 3 hours at 50–55° C. and then the reaction mass was diluted with sulfuric acid and with water to obtain 55% sulfuric acid. The precipitate was separated by filtration and washed with acetic acid. Yield, 1.2 g of compound which corresponds to the products from the example 1c of the structural formula

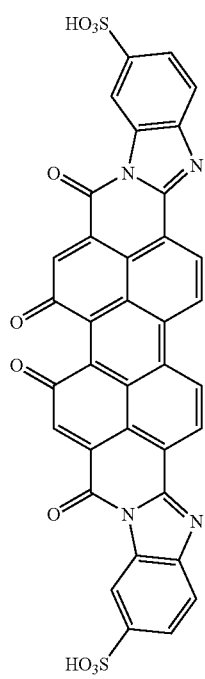
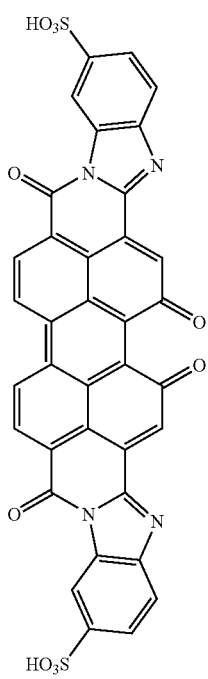

EXAMPLE 7

Synthesis of Cis-DBI PTCA Dioxo-Sulfon-Disulfoacids

Stage 7a. Sulfonation of Cis-DBI PCTA Dioxo-Disulfoacid

The product of example 6 (1 g) was sulfonated in 50 ml of 65% oleum for 10 hours at 65° C. and then the reaction mass was diluted with sulfuric acid and then with water to obtain 45% sulfuric acid. The precipitate was separated by filtration and washed with acetic acid. Yield, 1 g of compounds which corresponds to the product from the example 2b of the structural formula

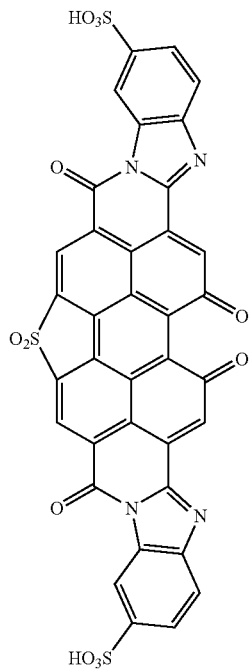
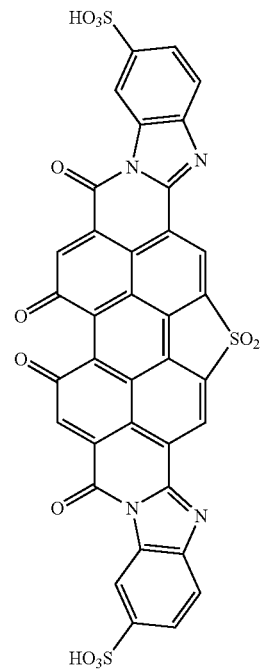

Stage 7b. Sulfonation of Cis-DBI PTCA

Cis-DBI PTCA (1 g) was sulfonated in 50 ml of 65% oleum for 12 hours at 60–55° C. and then the reaction mass was diluted with sulfuric acid and with water to obtain 65% sulfuric acid. The precipitate was separated by filtration and washed with acetic acid. Yield, 1.3 g of compound which corresponds to one of product from the example 7a.

EXAMPLE 8

Synthesis of Isomeric OXO-Disulfonic Acids Of PTCA DBI From DihydroxyPTCA

Stage 8a. Condensation of 2,8-dihydroxyPTCADA with o-phenylenediamine

A suspension of 1.5 g of dihydroxyPTCADA and 3 g of o-phenylenediamine in 30 ml of acetic acid was boiled for 8 hours. The precipitate was separated by filtration and washed with ethanol. Yield, 1.8 g of compounds of the structural formulas

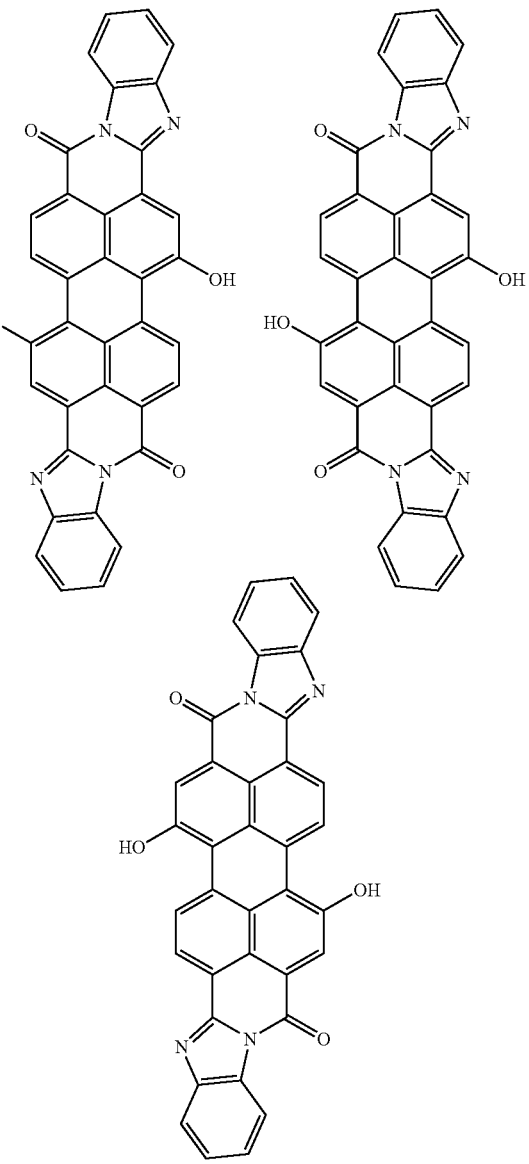

Mass spectrum (VISION 2000, negative reflection mode): m/z, 567.4; mol. wt., 568.5; elemental analysis, found (%): C, 75.82; 75; 91; H, 2.94; 2.65; N, 9.61; 9.49 $C_{36}H_{14}N_4O_{10}S_3$; anal. calcd. for $C_{36}H_{16}N_4O_4$ (%): C, 76.05; H, 2.84; N, 9.85; O, 11.6.

Stage 8b. Sulfonation of the Product of DihydroxyPTCADA Condensation with o-phenylenediamine The product of stage 1a (1 g) was sulfonated in 5 ml of 4% oleum for 12 hours at 100° C. and then the reaction mass was diluted with 20 ml of water. The precipitate was separated by filtration and washed with acetic acid. Yield, 1 g of compounds of the structural formulas

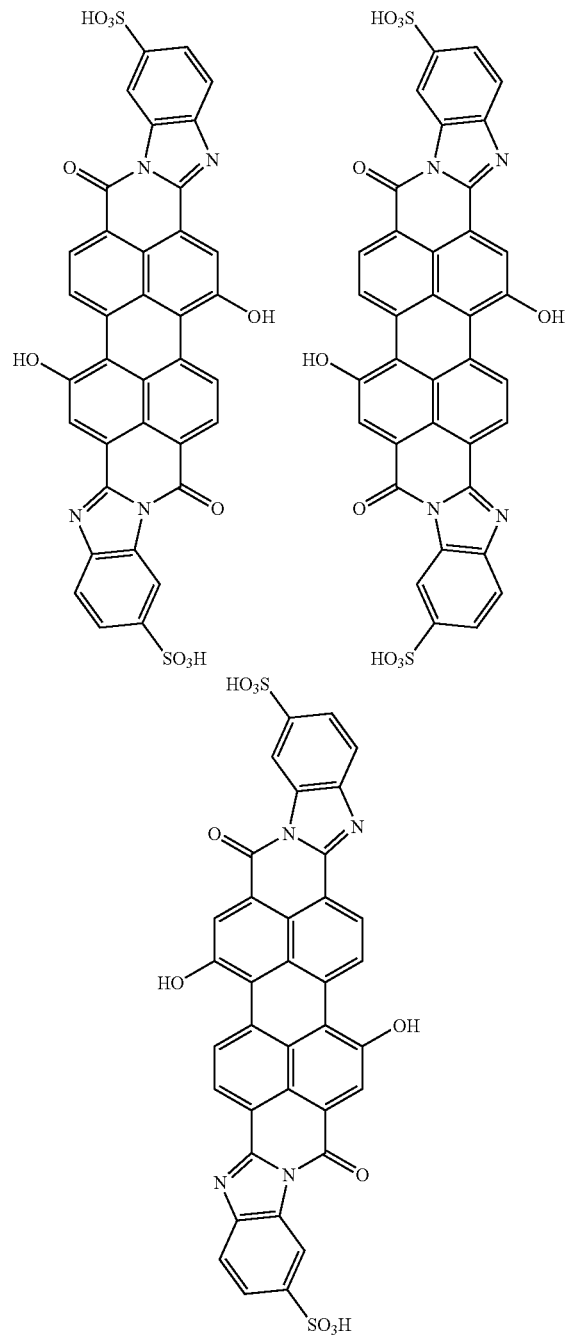

Mass spectrum (VISION 2000, negative reflection mode): m/z, 729.0; mol. wt., 728.6.

Stage 8c. Oxidation of dihydroxyPTCADBI Disulfoacids with Oleum

The product of stage 8b (1 g) was charged in 20 ml of 80% oleum and stirred for 12 hours at 20° C. and then the reaction mass was diluted to 50% sulfuric acid concentration. The precipitate was separated by filtration and washed with acetic acid. Yield, 0.8 g of compounds of the structural formulas

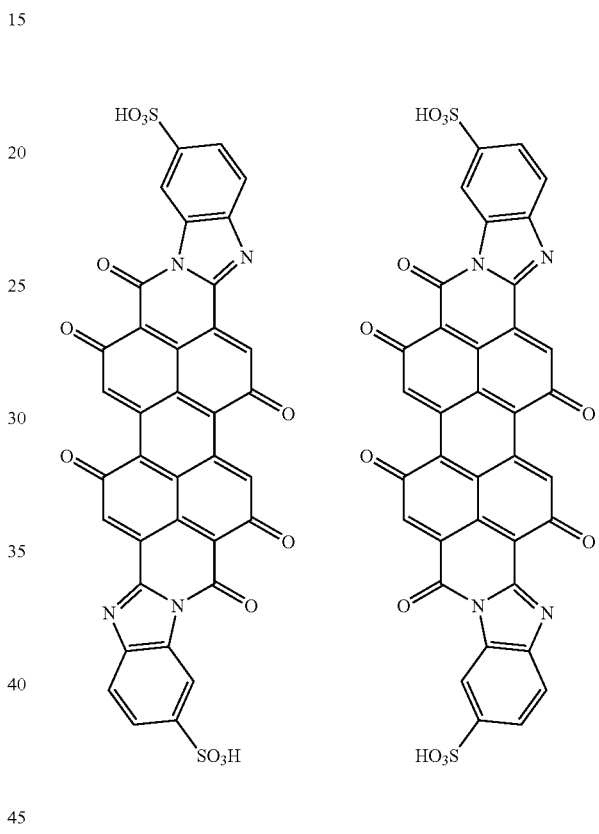

Mass spectrum (VISION 2000, negative reflection mode): m/z, 758.4; mol. wt., 758.6; elemental analysis, found (%): C, 56.62; 56; 84; H, 1.94; 1.72; N, 7.34; 7.32; S, 8.32; 8.40 $C_{36}H_{14}N_4O_{10}S_3$; anal. calcd. for $C_{36}H_{14}N_4O_{12}S_2$ (%): C, 56.99; H, 1.86; N, 7.39; O, 25.31; S, 8.45; IR spectrum (FSM-1201 Fourier-transform IR spectrometer, thin film on KRS-5 window) (ν, cm-1): 1230.4, 1180.5 (sulfonic groups), 1074.0, 1030.5 (sulfonic groups), 1700.9 (carbonyl); electronic absorption spectrum (Ocean PC2000, aqueous solution) (λmax, nm): 560.

Stage 8d. Condensation of 1,12-dihydroxyPTCADA with o-phenylenediamine

A suspension of 1.5 g of 1,12-dihydroxyPTCADA and 3 g of o-phenylene diamine in 30 ml of acetic acid was boiled for 8 hours. The precipitate was separated by filtration and washed with ethanol. Yield, 1.8 g of compounds of the structural formulas

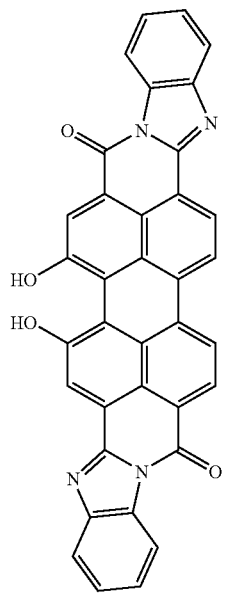
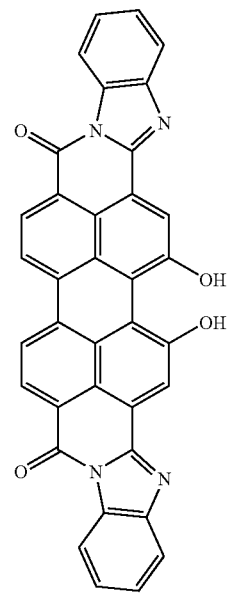

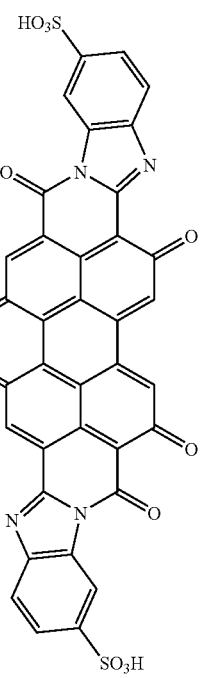
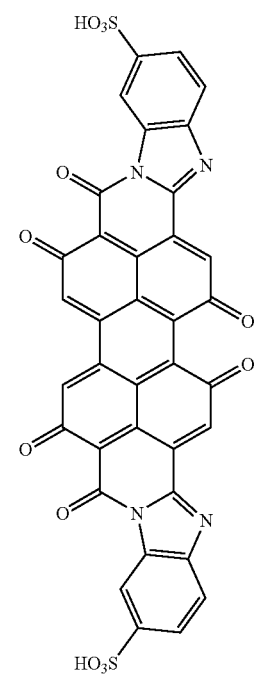

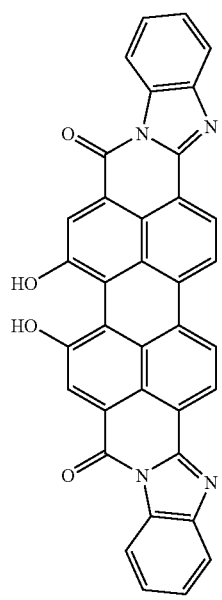

Mass spectrum (VISION 2000, negative reflection mode): m/z, 567.4; mol. wt., 568.5.

Stage 8e. Oxidation of dihydroxyPTCADBI Disulfoacids with Oleum

The product of stage 8d (1 g) was stirred in 10 ml of 80% oleum for 12 hours at 20° C. and then the reaction mass was diluted to 50% sulfuric acid concentration. The precipitate was separated by filtration and washed with acetic acid. Yield, 0.8 g of compounds of the structural formulas Mass spectrum (VISION 2000, negative reflection mode): m/z, 758.4; mol. wt., 758.6; elemental analysis, found (%): C, 56.54; 56; 77; H, 1.80; 1.74; N, 7.25; 7.30; S, 8.24; 8.36 $C_{36}H_{14}N_4O_{10}S_3$; anal. calcd. for $C_{36}H_{14}N_4O_{12}S_2$ (%): C, 56.99; H, 1.86; N, 7.39; O, 25.31; S, 8.45; IR spectrum (FSM-1201 Fourier-transform IR spectrometer, thin film on KRS-5 window) (ν, cm−1): 1230.4, 1180.5 (sulfonic groups), 1074.0, 1030.5 (sulfonic groups), 1700.9 (carbonyl); electronic absorption spectrum (Ocean PC2000, aqueous solution) (λmax, nm): 560.

Stage 8j. Sulfonation of the Product of DihydroxyPTCADA Condensation with o-phenylenediamine The reaction mass of stage 8e in 80% oleum was diluted to 50% oleum and heated for 10 hours at 50° C. and then was diluted with 200 ml of water. The precipitate was separated by filtration and washed with acetic acid. Yield, 1.4 g of compounds of the structural formulas

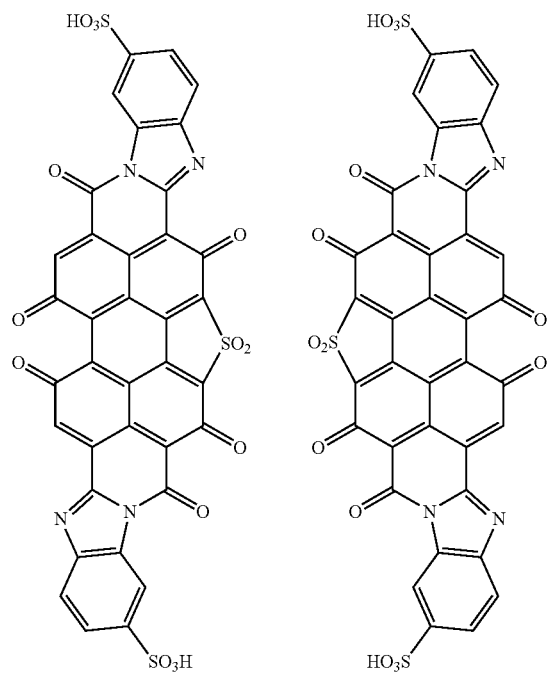
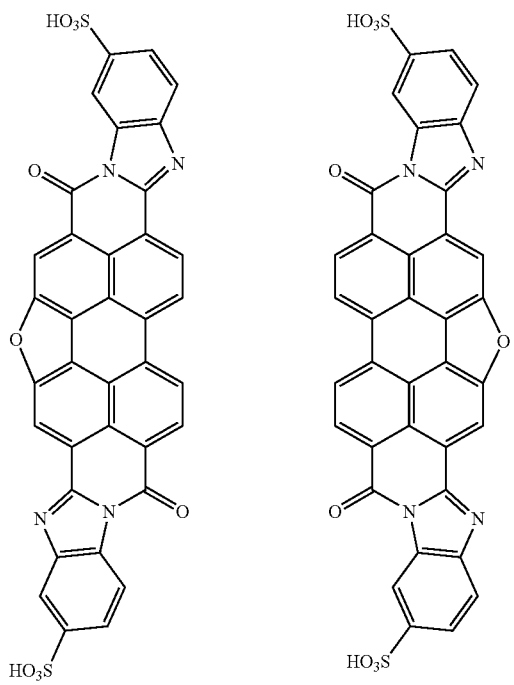

Mass spectrum (VISION 2000, negative reflection mode): m/z, 819.8; mol. wt., 818.7; elemental analysis, found (%): C, 52.77; 52; 80; H, 1.04; 1.26; N, 6.51; 6.49; S, 11.62; 11.40 $C_{36}H_{14}N_4O_{10}S_3$; anal. calcd. for $C_{36}H_{10}N_4O_{14}S_3$ (%): C, 52.81; H, 1.23; N, 6.84; O, 27.36; S, 11.75; IR spectrum (FSM-1201 Fourier-transform IR spectrometer, thin film on KRS-5 window) (ν, cm–1): 1230.4, 1180.5 (sulfonic groups), 1074.0, 1030.5 (sulfonic groups), 1330.0 (sulfone), 1700.6 (carbonyl); electronic absorption spectrum (Ocean PC2000, aqueous solution) (λmax, nm): 560, 675.

EXAMPLE 9

Synthesis Of PTCA DBI Furane Derivatives by Sulfonation of PTCA DBI

Stage 9a. Synthesis of Disulfonic Acid of Cis-PTCA DBI Furane

The product from the stage 8d (5.0 g), was introduced by portions into 35 ml of 10% oleum and sulfonated for 5 hours at 60° C. Then the reaction mass was sequentially diluted, first with 92% aqueous sulfuric acid to monohydrate and then with water to a sulfuric acid concentration of 65%. The precipitate was separated by filtration, triply resuspended in acetic acid, and dried to obtain 6.5 g of a compound of the structural formula

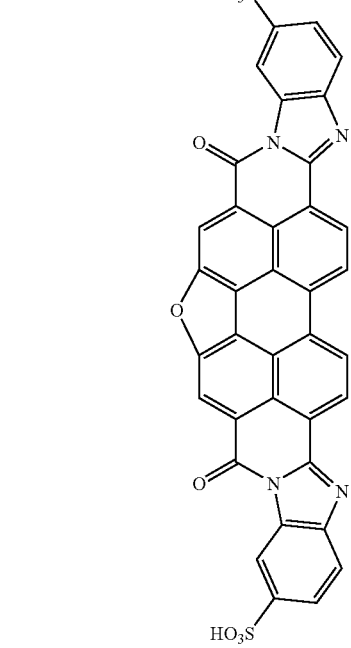

Mass spectrum (VISION 2000, negative reflection mode): m/z, 709.4; mol. wt., 710.65; elemental analysis, found: C, 60.66; 60.10; H, 2.09; 2.27; N, 7.39; 7.32; S, 9.51; 9.41 $C_{36}H_{14}N_4O_9S_2$; anal. calcd. for $C_{36}H_{14}N_4O_9S_2$ (%): C, 60.84; H, 1.99; N, 7.88; O, 20.26; S, 9.02; electronic absorption spectrum (Ocean PC2000, aqueous solution) (λmax, nm): 325, 355, 375, 600.

Stage 9b. Sulfonation of Disulfonic Acid of
Cis-PTCA DBI Furane with Oleum

The product of stage 9a (1 g) was charged in 30 ml of 50% oleum at 50° C. and stirred at this temperature for 8 hours. Then the reaction mass was diluted to the sulfuric acid concentration 65%. The precipitate was separated by filtration and washed with acetic acid. Yield, 0.4 g of compounds of the structural formulas

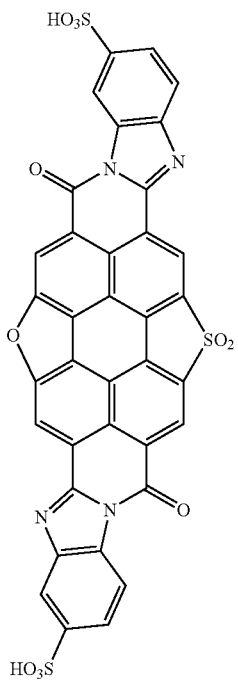

The mother liquid was diluted with water to sulfuric acid concentration 40%. The precipitate was separated by filtration and washed with acetic acid. Yield, 0.4 g of compounds of the structural formulas

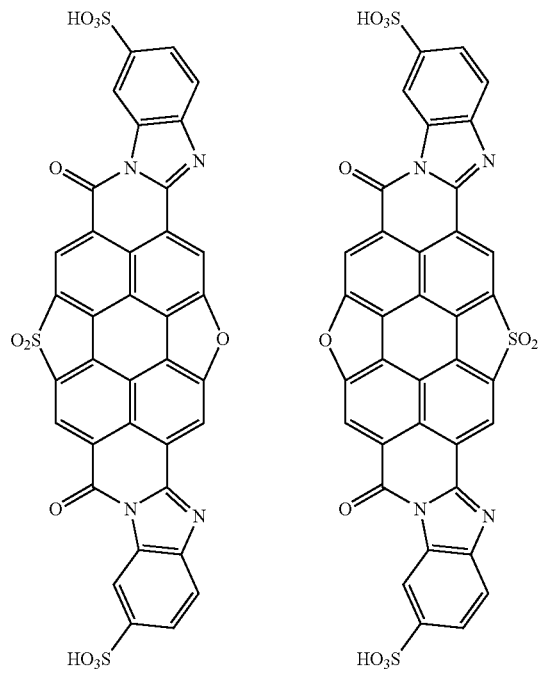

Mass spectrum (VISION 2000, negative reflection mode): m/z, 772.0 740.6; mol. wt., 772.7; elemental analysis, found (%): C, 55.56; 55.59 58.72; 58, 10; H, 1.49; 1.43 1.54; 1.56; N, 6.98, 6.83 7.31; 7.39; S, 13.00, 13.16 8.33; 8.46 $C_{36}H_{14}N_4O_{10}S_3$; anal. calcd. for $C_{36}H_{12}N_4O_{11}S_3$ (%): C, 55.96 58.38; H, 1.57 1.63; N, 7.25 7.5; O, 22.78 23.76; S, 12.45 8.66; IR spectrum (FSM-1201 Fourier-transform IR spectrometer, thin film on KRS-5 window) (ν, cm−1): 1230.0, 1182.2 (sulfonic groups), 1072.0, 1030.5 (sulfonic groups), 1324.0 (sulfone), 1700.0 (carbonyl); electronic absorption spectrum (Ocean PC2000, aqueous solution) (λmax, nm): 325, 375, 540 for the first fraction and 325, 355, 375, 535 for the second one.

The other derivatives corresponding to structures I through VI can be synthesized by analogous procedures, either through sulfonation of PTCA DBI isomers or mixtures, or by condensation of the corresponding PTCA derivatives followed by sulfonation, or by condensation of the PTCA derivatives with o-phenylenediamine sulfonate.

EXAMPLE 10

Obtaining a Liquid Crystal Composition and Film of PTCA DBI Dioxodisulfonic Acid and Determining the Optical Characteristics of the Film A solution of 10 g of a PTCA DBI dioxodisulfonic acid (Example 1, Stage c) in 79.9 ml of deionized water was prepared by stirring at 20° C. and neutralized by ammonia to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by the transmission spectra measured on a Cary-500 spectrophotometer in a wavelength range from 190 to 800 nm using a light beam polarized along the direction of film application (Tpar) and in the perpendicular direction (Tper) relative to the solution application direction. At a wavelength of λ=540 nm corresponding to maximum absorption, the dichroic ratio Kd=log(Tper)/log (Tpar) was equal to 32; at a film transmission of 35%, the contrast ratio (CR) was 170.

EXAMPLE 11

Obtaining a Liquid Crystal Composition and Film of a Mixture of PTCA DBI Dioxo- And Tetraoxo-Disulfoderivatives and Determining the Optical Characteristics of the Film A solution of 10 g of a mixture of PTCA DBI sulfoderivatives, including Dioxo-Disulfoderivative (Example 1, 30 mass %), Dioxo-Sulfon-Disulfoderivatives (Example 2b, 30 mass %), Tetraoxo-Disulfoderivatives (Example 8e, 20 mass %, Example 8j, 20 mass % ) and in 79.9 ml of deionized water was prepared by stirring at 20° C. and neutralized by ammonia. To this solution was added a solution of 0.1 g of sulfonol in 10 ml of water and the mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by the transmission spectra measured on a Cary-500 spectrophotometer in a wavelength range from 190 to 800 nm using a light beam polarized along the direction of film application (Tpar) and in the perpendicular direction (Tper) relative to the solution application direction. At a wavelength of λ=540 nm corresponding to maximum absorption, the dichroic ratio Kd=log(Tper)/log(Tpar) was equal to 28; at a film transmission of 36%, the contrast ratio (CR) was 150.

EXAMPLE 12

Obtaining a Liquid Crystal Composition and Film of a Mixture Of PTCA DBI Dioxo-Disulfoderivatives and Dioxo-Sulfon-Disulfoderivatives with Indanthrone Derivatives and Determining the Optical Characteristics of the Film A solution of 10 g of a mixture of PTCA DBI Dioxo-Disulfoderivatives (Example 1, 20 mass %), Dioxo-Sulfon-Disulfoderivatives (Example 2b, 20 mass %) and indanthrone trisulfonic acid (60 mass %) in 79.9 ml of deionized water was prepared by stirring at 20° C. and neutralized by ammonia. To this solution was added a solution of 0.1 g of sulfonol in 10 ml of water and the mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by the transmission spectra measured on a Cary-500 spectrophotometer in a wavelength range from 190 to 800 nm using a light beam polarized along the direction of film application (Tpar) and in the perpendicular direction (Tper) relative to the solution application direction. At a wavelength of λ=650 nm corresponding to maximum absorption, the dichroic ratio Kd=log(Tper)/log(Tpar) was equal to 35; at a film transmission of 35%, the contrast ratio (CR) was 250.

EXAMPLE 13

Obtaining a Liquid Crystal Composition and Film of a Mixture of PTCA DBI Dioxo-Sulfon-Disulfoderivatives with Derivatives of Indanthrone and Naphthalenetetracarboxylic Acid and Determining the Optical Characteristics of the Film A solution of 10 g of a mixture including PTCA DBI Dioxo-Sulfon-Disulfoderivatives (Example 2b, 40 mass %), indanthrone trisulfonic acid (40 mass %), and NTCA DBI disulfonic acid (20 mass %) in 79.9 ml of deionized water was prepared by stirring at 20° C. and neutralized by ammonia. To this solution was added a solution of 0.1 g of sulfonol in 10 ml of water and the mixture was thoroughly stirred to obtain 100 g of a 10% liquid crystal solution. This solution was applied onto a quartz glass plate with a Meyer rod No. 3 at a linear velocity of 25 mm/s. The process was conducted at a temperature of 20° C. and a relative humidity of 65%, after which the film was dried under the same conditions.

The film was characterized by the transmission spectra measured on a Cary-500 spectrophotometer in a wavelength range from 190 to 800 nm using a light beam polarized along the direction of film application (Tpar) and in the perpendicular direction (Tper) relative to the solution application direction. At a wavelength of λ=650 nm corresponding to maximum absorption, the dichroic ratio Kd=log(Tper)/log(Tpar) was equal to 34; at a film transmission of 35%, the contrast ratio (CR) was 200.

All compounds characterized by the structural formula I through VI give stable lyotropic liquid crystal systems which can be used for obtaining optically anisotropic films with high performance characteristics and high reproducibility. The above examples are illustrative and are should not be interpreted as limiting the scope of the present invention.

What is claimed is:

1. A sulfonated perylenetetracarboxylic acid dibenzimidazole (PTCA DBI) compound containing an even number of oxo-groups pendant to a perylene core where the oxo-groups and portions of the perylene core form a para-quinoid system of bonds.

2. A sulfonated perylenetetracarboxylic acid dibenzimidazole (PTCA DBI) compound containing oxo-groups pendant to a perylene core where the oxo-groups and portions of the perylene core form a para-quinoid system of bonds, wherein said compound comprises one of the following structures I to IV:

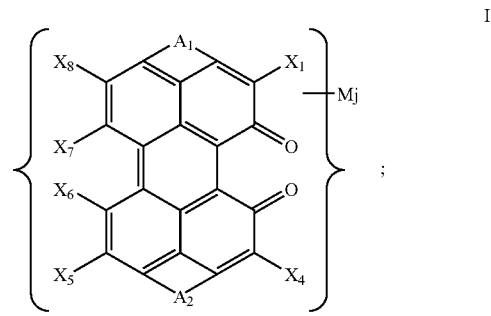

I

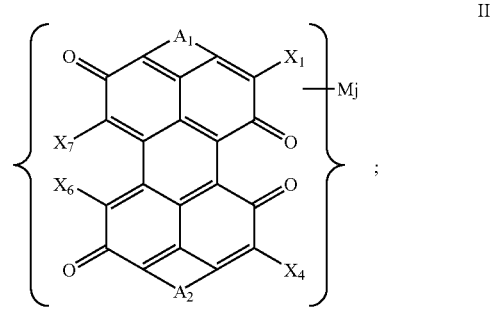

II

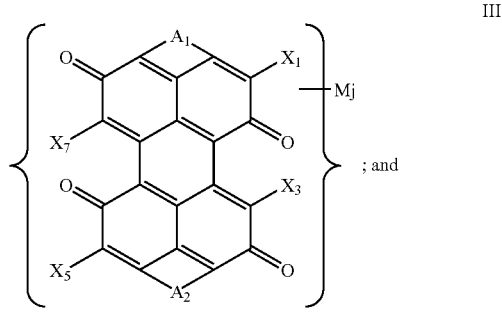

III

; and

-continued

IV

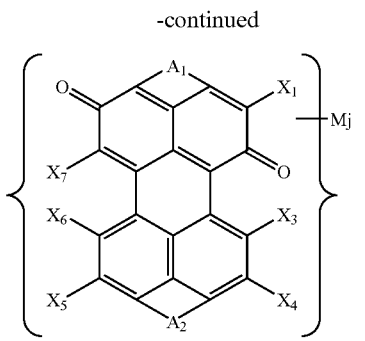

where $A_1$ and $A_2$ are, independently, identical or non-identical fragments comprising the following structural formula

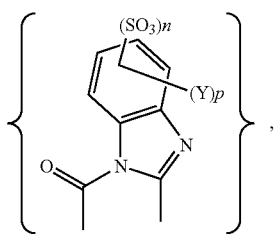

where $X_1$, $X_3$, $X_4$, $X_5$, $X_6$, $X_7$, and $X_8$ are substituents selected, independently, from —H, —OH, and —SO$_3$H, where each Y is a substituents selected, independently, from —H, —Cl, —F, —Br, alkyl, —OH, oxyalkyl, —NO$_2$, and NH$_2$, where n is an integer selected from 0, 1, and 2, such that at least one of fragments $A_1$ and $A_2$ comprise at least one sulfo group, where p is an integer selected from 0, 1, 2, 3 and 4, where each M is a counterion and, when n>1, each M can be the same or different, and where j is the number of counterions in the molecule and can be fractional if one or more of the counterions belong to several molecules.

3. A sulfonated perylenetetracarboxylic acid dibenzimidazole (PTCA DBI) compound containing oxo-groups pendant to a perylene core where the oxo-groups and portions of the perylene core form a para-quinoid system of bonds wherein said compound comprises one of the following structures V to VII:

V

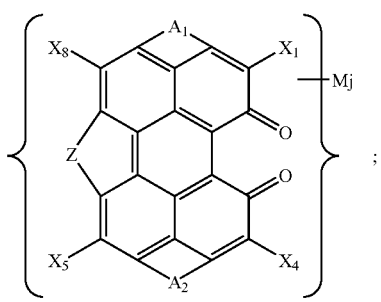

VI

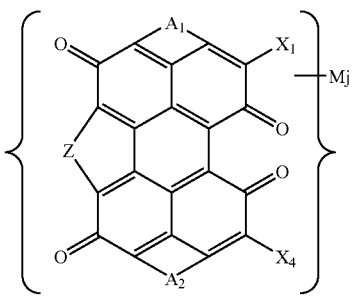

; and

VII

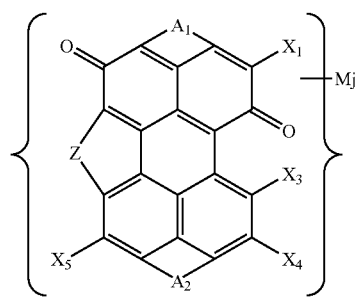

where $A_1$ and $A_2$ are, independently, identical or non-identical fragments comprising the following structural formula

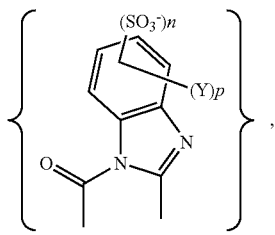

where $X_1$, $X_3$, $X_4$, $X_5$, $X_6$, $X_7$, and $X_8$ are substituents selected, independently, from —H, —OH, and —SO$_3$H, where Z is divalent bridge chosen from —O—, —SO$_2$—, and —O—SO$_2$—, where each Y is a substituent selected, independently, from —H, —Cl, —F, —Br, alkyl, —OH, oxyalkyl, —NO$_2$, and —NH$_2$, where n is an integer selected from 0, 1, and 2, such that at least one of fragments $A_1$ and $A_2$ comprises at least one sulfo group, where p is an integer selected from 0, 1, 2, 3 and 4, where each M is a counterion and, when n>1, each M can be the same or different, and where j is the number of counterions in the molecule, which can be fractional if one or more counterions belong to several molecules.

4. The sulfonated oxo substituted PTCA DBI compound according to either of claim 2 or 3, where said compound is capable of forming a stable lyotropic liquid crystal system.

5. The sulfonated oxo substituted PTCA DBI compound according to either of claim 2 or 3, where said compound is capable of forming optically isotropic or anisotropic films.

6. The sulfonated oxo substituted PTCA DBI compound according to either of claim 2 or 3, where said compound is capable of forming at least partially crystalline films.

7. A lyotropic liquid crystal system comprising at least one sulfonated perylenetetracarboxylic acid dibenzimidazole (PTCA DBI) compound containing an even number of oxo-groups pendant to a perylene core where the oxo-groups and portions of the perylene core form a para-quinoid system of bonds.

8. A lyotropic liquid crystal system comprising at least one sulfonated perylenetetracarboxylic acid dibenzimidazole (PTCA DBI) compound containing oxo-groups pendant to a perylene core where the oxo-groups and portions of the perylene core form a para-quinoid system of bonds, wherein said compound comprises one of the following structures I through IV:

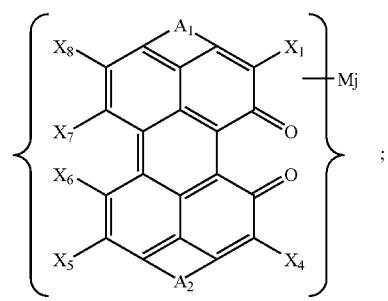

I

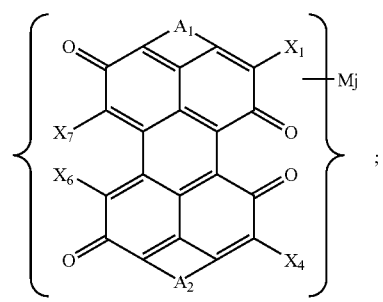

II

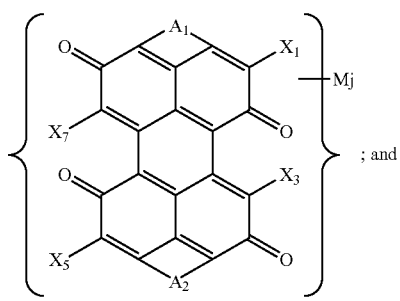

III

; and

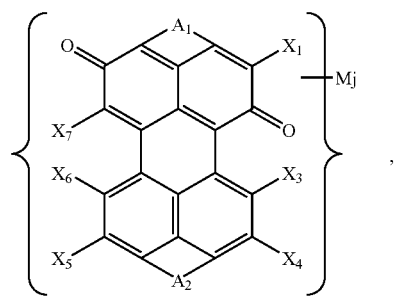

IV

, where $A_1$ and $A_2$ are, independently, identical or non-identical fragments comprising the following structural formula

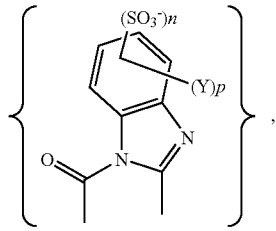

, where $X_1$, $X_3$, $X_4$, $X_5$, $X_6$, $X_7$, and $X_8$ are substituents selected, independently, from —H, —OH, and —SO$_3$H,.

where each Y is a substituent selected, independently, from —H, —Cl, —F, —Br, alkyl, —OH, oxyalkyl, —NO$_2$, and —NH$_2$, where n is an integer selected from 0, 1, and 2, such that at least one of fragments $A_1$ or $A_2$ comprises at least one sulfo group, where p is an integer selected from 0, 1, 2, 3 and 4, where each M is a counterion and, when n>1, each M can be the same or different, and where j is the number of counterions in the molecule, which can be fractional if one or more counterions belong to several molecules.

9. A lyotropic liquid crystal system comprising at least one sulfonated perylenetetracarboxylic acid dibenzimidazole compound containing oxo-groups pendant to a perylene core where the oxo-groups and portions of the perylene core form a para-quinoid system of bonds, wherein said compound comprises one of the following structures V to VII:

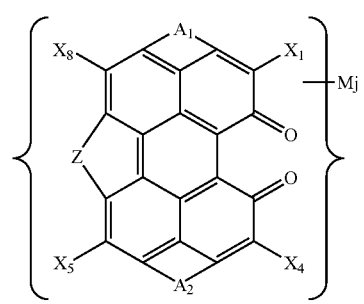

V

;

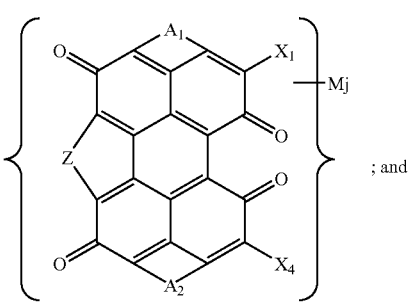

VI

; and

-continued

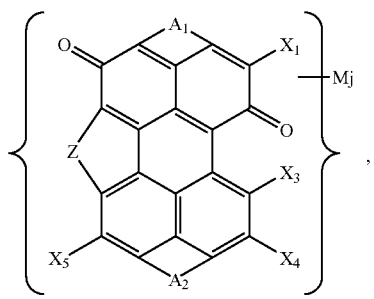
VII where A₁ and A₂ are, independently, identical or non-identical fragments comprising the following structural formula

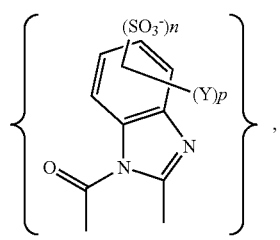

where $X_1$, $X_3$, $X_4$, $X_5$, $X_6$, $X_7$, and $X_8$ are substituents selected, independently, from —H, —OH, and —SO₃H, where Z is a bridge chosen from —O—, —SO₂—, and —O—SO₂—, where each Y is a substituent selected, independently, from —H, —Cl, —F, —Br, alkyl, —OH, oxyalkyl, —NO₂, and NH₂ where n is an integer selected from 0, 1, and 2, such that at least one of fragments A₁ and A₂ comprises at least one sulfo group, where p is an integer selected from 0, 1, 2, 3 and 4, where each M is a counterion and, when n>1, each M can be the same or different, and where j is the number of counterions in the molecule, which can be fractional if one or more counterions belong to several molecules.

10. The lyotropic liquid crystal system according to claim 7, wherein said system is aqueous.

11. The lyotropic liquid crystal system according to claim 7, wherein said system is comprises a mixture of water and an organic solvent miscible with water.

12. The lyotropic liquid crystal system according to claim 7, wherein the content of sulfonated oxo substituted PTCA DBI compounds in said liquid crystal system ranges from 3 to 40 mass %.

13. The lyotropic liquid crystal system according to claim 7, further comprising up to 5% mass of surfactants.

14. The lyotropic liquid crystal system according to claim 7, further comprising up to 5% mass plasticizers.

15. The lyotropic liquid crystal system according to claim 7, comprising a mixture of sulfonated oxo substituted PTCA DBI compounds comprising any of the following structures I to VII:

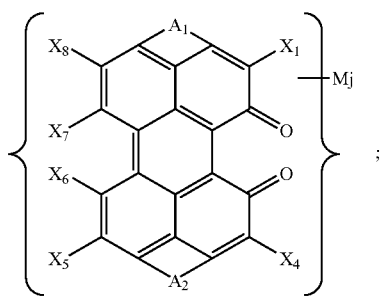
I

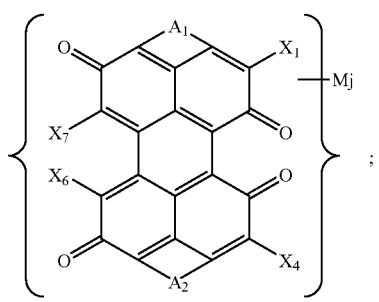
II

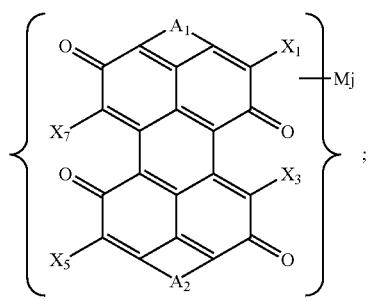
III

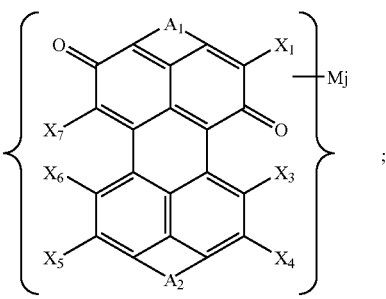
IV

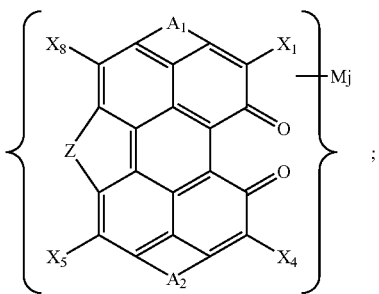
V

-continued

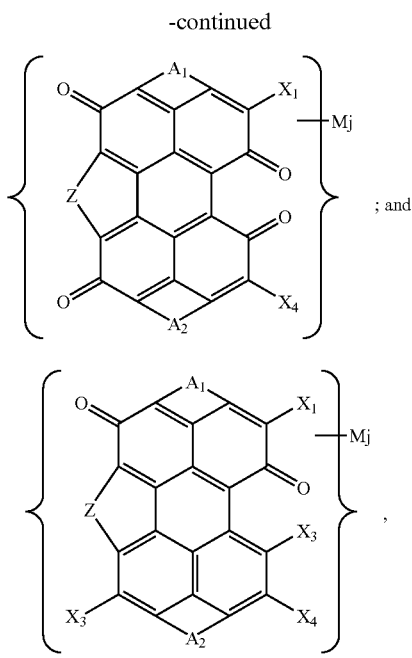

where $A_1$ and $A_2$ are, independently, identical or non-identical fragments comprising the following structural formula

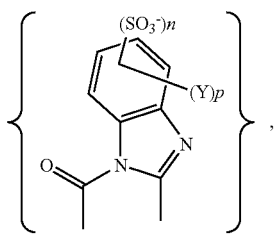

where $X_1$, $X_3$, $X_4$, $X_5$, $X_6$, $X_7$, and $X_8$ are substituents selected, independently, from —H, —OH, and —SO$_3$H, where Z is a divalent bridge chosen from —O—SO$_2$—, and —O—, —SO$_2$—, where each Y is a substituent selected, independently, from —H, —Cl, —F, —Br, alkyl, —OH, oxyalkyl, —NO$_2$, and —NH$_2$, where n is an integer selected from 0, 1, and 2, such that at least one of fragments $A_1$ and $A_2$ comprises at least one sulfo group, where p is an integer selected from 0, 1, 2, 3 and 4, where each M is a counterion and, when n>1, each M can be the same or different, where j is the number of counterions in the molecule, which can be fractional if one or more counterions belong to several molecules, where compounds of structural formula I and/or V are present in a concentration range of approximately 0 to 99% by mass, where compounds of structural formula II and/or VI are present in a concentration range of approximately 0 to 99% by mass, where compounds of structural formula IV and/or VII are present in a concentration range of approximately 0 to 50% by mass, and where compounds of structural formula III are present in a concentration range of approximately 0 to 99% by mass, wherein the total amount of formulas I to VII is 100% by mass.

16. The lyotropic liquid crystal system according to claim 15, wherein compounds of structural formula I and/or V are present in a concentration range of approximately 0 to 70% by mass, compounds of structural formula II and/or VI are present in a concentration range of approximately 0 to 50% by mass, compounds of structural formula IV and/or VII are present in a concentration range of approximately 0 to 20% by mass, and compounds of structural formula III are presented in a concentration range of approximately 0 to 50% by mass, wherein the total amount of formulas I to VII is 100% by mass.

17. The lyotropic liquid crystal system according to either of claim 8 or 9, further comprising at least one additional sulfonated oxo substituted PTCA DBI compound comprising one of the following structures VIII to X:

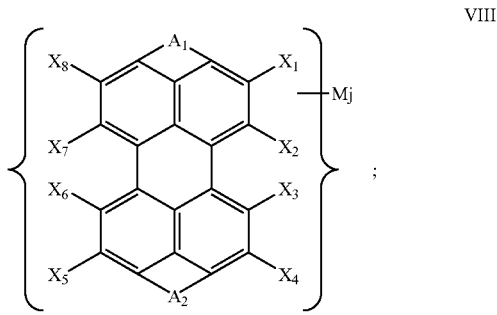

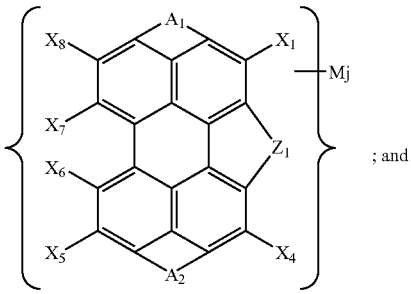

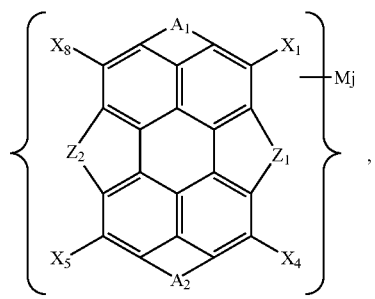

where $A_1$ and $A_2$ are, independently, identical or non-identical fragments comprising the following structural formula

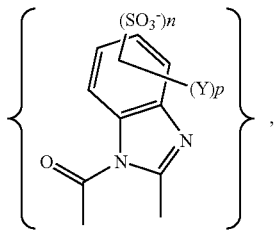

where $X_1$, $X_2$, $X_3$, $X_4$, $X_5$, $X_6$, $X_7$, and $X_8$ are substituents selected, independently, from —H, —OH, and —$SO_3H$, such that at least one of these substituents is different from —H and substituents $X_2$, $X_3$ and/or $X_6$, $X_7$ may interact with each other to form bridges $Z_1$ and/or $Z_2$, where $Z_1$ and/or $Z_2$ are bridges chosen, independently, from —O—, —$SO_2$—, and —$SO_2$—O—, where each Y is a substituent selected, independently, from —H, —Cl, —F, —Br, alkyl, —OH, oxyalkyl, —$NO_2$, and —$NH_2$, where n is an integer selected from 0, 1, and 2, such that at least one of fragments $A_1$ and $A_2$ comprises at least one sulfo group where p is an integer selected from 0, 1, 2, 3 and 4 where each M is counterion and, when n>1, each M can be the same or different, and where j is the number of counterions in the molecule, which can be fractional if one or more counterions belong to several molecules.

18. The lyotropic liquid crystal system according to claim 7, further comprising at least one water-soluble organic dye or an organic compound capable of participating in the formation of a common lyotropic liquid crystal system with the sulfonated oxo substituted PTCA DBI compound.

19. An optically anisotropic film comprising at least one sulfonated perylenetetracarboxylic acid dibenzimidazole (PTCA DBI) compound containing an even number of oxo-groups pendant to a perylene core where the oxo-groups and portions of the perylene core form a para-quinoid system of bonds.

20. The optically anisotropic film according to claim 19, wherein said film is formed by depositing a lyotropic liquid crystal system comprising the sulfonated oxo substituted PTCA DBI compound.

21. The optically anisotropic film according to claim 19, wherein said film is at least partially crystalline.

22. The optically anisotropic film of claim 21, wherein the interplanar spacing in the crystals along one of the optical axes is in the range of approximately 3.1 Å to 3.7 Å.

23. The optically anisotropic film according to claim 19, comprising a mixture of sulfonated oxo substituted PTCA DBI compounds comprising any one of the following structures I to VII:

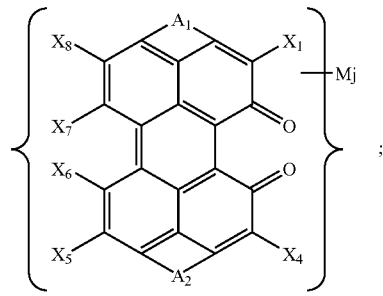

I

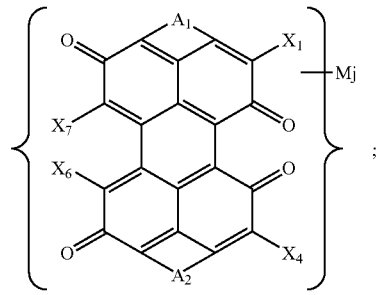

II

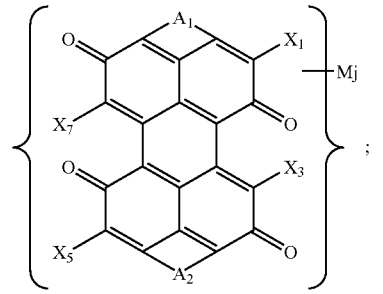

III

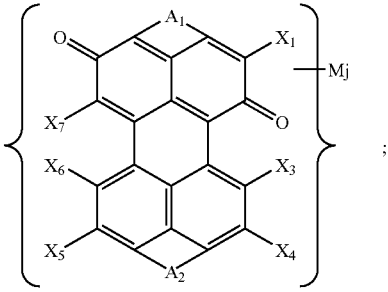

IV

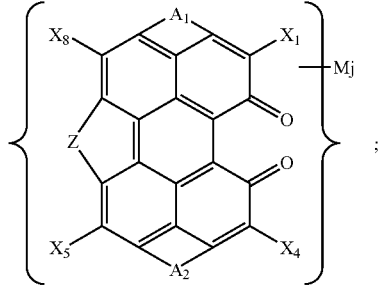

V

-continued

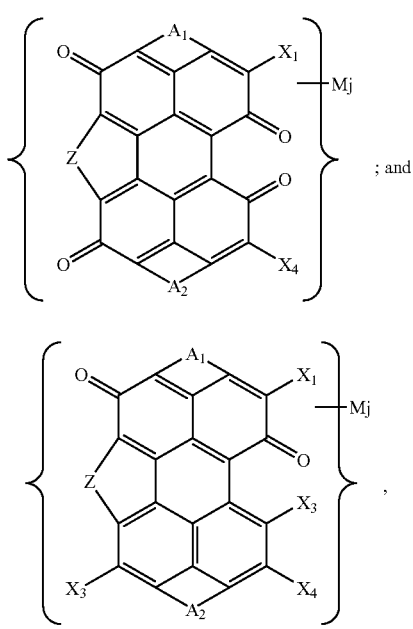

where $A_1$ and $A_2$ are, independently, identical or non-identical fragments comprising the following structural formula

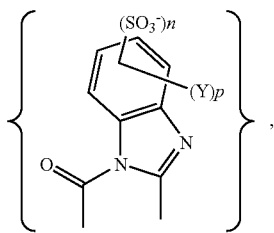

where $X_1$, $X_3$, $X_4$, $X_5$, $X_6$, $X_7$, and $X_8$ are substituents selected, independently, from —H, —OH, and —SO$_3$H,
where Z is bridge chosen from —O—, —SO$_2$—, and —O—SO$_2$—,
where each Y is a substituent selected, independently, from —H, —Cl, —F, —Br, alkyl, —OH, oxyalkyl, —NO$_2$, and —NH$_2$, where n is an integer selected from 0, 1, and 2, such that at least one of fragments $A_1$ and $A_2$ comprises at least one sulfo group, where p is an integer selected from 0, 1, 2, 3 and 4, where each M is a counterion and, when n>1, each M can be the same or different, where j is the number of counterions in the molecule, which can be fractional if one or more counterions belongs to several molecules, where compounds of structural formula I and/or V are present in a concentration range of approximately 0 to 99% by mass, where compounds of structural formula II and/or VI are present in a concentration range of approximately 0 to 99% by mass, where compounds of structural formula IV and/or VII are present in a concentration range of approximately 0 to 50% by mass, and where compounds of structural formula III are present in a concentration range of approximately 0 to 99% by mass, wherein the total amount of formulas I to VII is 100% by mass.

24. The optically anisotropic film according to claim 23, wherein compounds of structural formula I and/or V are present in a concentration range of approximately 0 to 70% by mass, compounds of structural formula II and/or VI are present in a concentration range of approximately 0 to 50% by mass, compounds of structural formula IV and/or VII are present in a concentration range of approximately 0 to 20% by mass, and compounds of structural formula III are present in a concentration range of approximately 0 to 50% by mass, wherein the total amount of formulas I to VII is 100% by mass.

25. The optically anisotropic film according to claim 19, further comprising at least one water-soluble organic dye.

26. The optically anisotropic film according to claim 19, wherein said film is polarizing.

27. The optically anisotropic film according to claim 19, wherein said film is a retarder.

* * * * *